US008660647B2

(12) United States Patent
Parnis et al.

(10) Patent No.: US 8,660,647 B2
(45) Date of Patent: Feb. 25, 2014

(54) STIMULATING CRANIAL NERVE TO TREAT PULMONARY DISORDER

(75) Inventors: Steven M. Parnis, Pearland, TX (US); Steven E. Maschino, Seabrook, TX (US); William R. Buras, Friendswood, TX (US); Albert W. Guzman, League City, TX (US)

(73) Assignee: Cyberonics, Inc., Houston, TX (US)

( * ) Notice: Subject to any disclaimer, the term of this patent is extended or adjusted under 35 U.S.C. 154(b) by 1492 days.

(21) Appl. No.: 11/191,896

(22) Filed: Jul. 28, 2005

(65) Prior Publication Data
US 2007/0027496 A1    Feb. 1, 2007

(51) Int. Cl.
*A61N 1/00*    (2006.01)

(52) U.S. Cl.
USPC .................................. 607/42; 607/9

(58) Field of Classification Search
USPC ........................................ 607/2, 9, 42
See application file for complete search history.

(56) References Cited

U.S. PATENT DOCUMENTS

| 4,305,402 | A | 12/1981 | Katims |
| 4,338,945 | A | 7/1982 | Kosugi et al. |
| 4,431,000 | A | 2/1984 | Butler et al. |
| 4,503,863 | A | 3/1985 | Katims |
| 4,556,064 | A | 12/1985 | Pomeranz et al. |
| 4,573,481 | A | 3/1986 | Bullara |
| 4,590,946 | A | 5/1986 | Loeb |
| 4,598,713 | A | 7/1986 | Hansjurgens et al. |
| 4,702,254 | A | 10/1987 | Zabara |
| 4,793,353 | A | 12/1988 | Borkan |
| 4,867,164 | A | 9/1989 | Zabara |
| 5,025,807 | A | 6/1991 | Zabara |
| 5,154,172 | A | 10/1992 | Terry, Jr. et al. |
| 5,188,104 | A | 2/1993 | Wernicke et al. |
| 5,199,428 | A | 4/1993 | Obel et al. |
| 5,199,430 | A | 4/1993 | Fang et al. |
| 5,215,086 | A | 6/1993 | Terry, Jr. et al. |
| 5,231,988 | A | 8/1993 | Wernicke et al. |
| 5,243,980 | A | 9/1993 | Mehra |

(Continued)

FOREIGN PATENT DOCUMENTS

| EP | 1486232 A2 | 12/2004 |
| WO | 9302744 A1 | 2/1993 |
| WO | 2005007120 A2 | 6/2005 |
| WO | 2005053788 A1 | 6/2005 |

OTHER PUBLICATIONS

Sjogren, M.D., Magnus et al.; Cognitive Effects of VNS Therapy in Patients with Alzheimer's Disease—Results of a One-Year Clinical Trial; 58th Annual Scientific Convention of the Society of Biological Psychiatry; May 15-17, 2003, San Francisco, CA.

(Continued)

*Primary Examiner* — Christopher D Koharski
*Assistant Examiner* — Michael D Abreu
(74) *Attorney, Agent, or Firm* — Cyberonics, Inc.

(57) ABSTRACT

A method for stimulating a portion of a vagus nerve of a patient to treat a pulmonary disorder is provided. At least one electrode is coupled to at least one portion of a left vagus nerve and/or a right vagus nerve of the patient. An electrical signal is applied to the portion of the vagus nerve using the electrode to treat the pulmonary disorder. The electrical signal may perform a blocking of an intrinsic neural activity on said at least one portion of the left vagus nerve and said right vagus nerve.

17 Claims, 13 Drawing Sheets

(56) References Cited

U.S. PATENT DOCUMENTS

| | | |
|---|---|---|
| 5,263,480 A | 11/1993 | Wernicke et al. |
| 5,269,303 A | 12/1993 | Wernicke et al. |
| 5,299,569 A | 4/1994 | Wernicke et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,356,425 A | 10/1994 | Bardy et al. |
| 5,411,531 A | 5/1995 | Hill et al. |
| 5,423,872 A | 6/1995 | Cigaina |
| 5,514,175 A | 5/1996 | Kim et al. |
| 5,540,730 A | 7/1996 | Terry, Jr. et al. |
| 5,540,734 A | 7/1996 | Zabara |
| 5,571,150 A | 11/1996 | Wernicke et al. |
| 5,611,350 A | 3/1997 | John |
| 5,645,570 A | 7/1997 | Corbucci |
| 5,658,318 A | 8/1997 | Stroetmann et al. |
| 5,683,422 A | 11/1997 | Rise et al. |
| 5,690,681 A | 11/1997 | Geddes et al. |
| 5,690,691 A | 11/1997 | Chen et al. |
| 5,700,282 A * | 12/1997 | Zabara .............................. 607/9 |
| 5,702,428 A | 12/1997 | Tippey et al. |
| 5,707,400 A | 1/1998 | Terry, Jr. et al. |
| 5,755,750 A | 5/1998 | Petruska et al. |
| 5,766,231 A | 6/1998 | Erickson et al. |
| 5,792,186 A | 8/1998 | Rise |
| 5,792,210 A | 8/1998 | Wamubu et al. |
| 5,836,994 A | 11/1998 | Bourgeois |
| 5,861,014 A | 1/1999 | Familoni |
| 5,861,022 A | 1/1999 | Hipskind |
| 5,913,876 A | 6/1999 | Taylor et al. |
| 5,916,239 A | 6/1999 | Geddes et al. |
| 5,919,216 A | 7/1999 | Houben et al. |
| 5,995,872 A | 11/1999 | Bourgeois |
| 6,002,966 A | 12/1999 | Loeb et al. |
| 6,006,134 A | 12/1999 | Hill et al. |
| 6,026,326 A | 2/2000 | Bardy |
| 6,073,048 A | 6/2000 | Kieval et al. |
| 6,083,249 A | 7/2000 | Familoni |
| 6,091,992 A | 7/2000 | Bourgeois et al. |
| 6,097,984 A | 8/2000 | Douglas |
| 6,104,955 A | 8/2000 | Bourgeois |
| 6,104,956 A | 8/2000 | Naritoku et al. |
| 6,109,269 A | 8/2000 | Rise et al. |
| 6,115,635 A | 9/2000 | Bourgeois |
| 6,141,590 A | 10/2000 | Renirie et al. |
| 6,152,953 A | 11/2000 | Hipskind |
| 6,161,044 A | 12/2000 | Silverstone |
| 6,216,039 B1 | 4/2001 | Bourgeois |
| 6,233,488 B1 | 5/2001 | Hess |
| 6,240,316 B1 | 5/2001 | Richmond et al. |
| 6,259,951 B1 | 7/2001 | Kuzma et al. |
| 6,266,564 B1 | 7/2001 | Hill et al. |
| 6,304,787 B1 | 10/2001 | Kuzma et al. |
| 6,308,104 B1 | 10/2001 | Taylor et al. |
| 6,327,503 B1 | 12/2001 | Familoni |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,366,814 B1 | 4/2002 | Boveja et al. |
| 6,374,140 B1 | 4/2002 | Rise |
| 6,381,499 B1 | 4/2002 | Taylor et al. |
| 6,438,423 B1 | 8/2002 | Rezai et al. |
| 6,449,512 B1 | 9/2002 | Boveja |
| 6,473,644 B1 | 10/2002 | Terry, Jr. et al. |
| 6,505,074 B2 | 1/2003 | Boveja et al. |
| 6,532,388 B1 | 3/2003 | Hill et al. |
| 6,542,774 B2 | 4/2003 | Hill et al. |
| 6,542,776 B1 | 4/2003 | Gordon et al. |
| 6,556,868 B2 | 4/2003 | Naritoku et al. |
| 6,564,101 B1 | 5/2003 | Zikria |
| 6,564,102 B1 | 5/2003 | Boveja |
| 6,587,719 B1 | 7/2003 | Barrett et al. |
| 6,587,727 B2 | 7/2003 | Osorio et al. |
| 6,600,953 B2 | 7/2003 | Flesler et al. |
| 6,606,518 B1 | 8/2003 | Cigaina |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,625,492 B2 | 9/2003 | Florio et al. |
| 6,628,987 B1 | 9/2003 | Hill et al. |
| 6,650,943 B1 | 11/2003 | Whitehurst et al. |
| 6,656,960 B2 | 12/2003 | Puskas |
| 6,668,191 B1 | 12/2003 | Boveja |
| 6,684,104 B2 | 1/2004 | Gordon et al. |
| 6,708,064 B2 | 3/2004 | Rezai |
| 6,721,603 B2 | 4/2004 | Zabara et al. |
| 6,735,474 B1 | 5/2004 | Loeb et al. |
| 6,735,475 B1 | 5/2004 | Whitehurst et al. |
| 6,754,536 B2 | 6/2004 | Swoyer et al. |
| 6,775,573 B2 | 8/2004 | Schuler et al. |
| 6,788,970 B1 | 9/2004 | Park et al. |
| 6,788,975 B1 | 9/2004 | Whitehurst et al. |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,889,076 B2 | 5/2005 | Cigaina |
| 6,895,278 B1 | 5/2005 | Gordon |
| 6,907,295 B2 | 6/2005 | Gross et al. |
| 6,908,487 B2 | 6/2005 | Cigaina |
| 6,961,618 B2 | 11/2005 | Osorio et al. |
| 7,050,856 B2 | 5/2006 | Stypulkowski |
| 7,904,159 B2 | 3/2011 | Errico et al. |
| 8,010,197 B2 | 8/2011 | Errico et al. |
| 8,041,428 B2 | 10/2011 | Errico et al. |
| 8,099,167 B1 | 1/2012 | Errico et al. |
| 2002/0016344 A1* | 2/2002 | Tracey ........................ 514/343 |
| 2002/0099417 A1 | 7/2002 | Naritoku et al. |
| 2002/0116030 A1 | 8/2002 | Rezai |
| 2003/0078623 A1* | 4/2003 | Weinberg et al. ................. 607/9 |
| 2003/0236558 A1 | 12/2003 | Whitehurst et al. |
| 2004/0176812 A1 | 9/2004 | Knudson et al. |
| 2004/0243182 A1* | 12/2004 | Cohen et al. ..................... 607/2 |
| 2005/0010262 A1 | 1/2005 | Rezai et al. |
| 2005/0021092 A1* | 1/2005 | Yun et al. ......................... 607/3 |
| 2005/0038484 A1 | 2/2005 | Knudson et al. |
| 2005/0049655 A1 | 3/2005 | Boveja et al. |
| 2005/0065553 A1* | 3/2005 | Ben Ezra et al. ................. 607/2 |
| 2005/0065562 A1 | 3/2005 | Rezai |
| 2005/0065573 A1 | 3/2005 | Rezai |
| 2005/0075701 A1 | 4/2005 | Shafer |
| 2005/0075702 A1 | 4/2005 | Shafer |
| 2005/0131467 A1 | 6/2005 | Boveja |
| 2005/0131485 A1 | 6/2005 | Knudson et al. |
| 2005/0131486 A1 | 6/2005 | Boveja et al. |
| 2005/0177192 A1 | 8/2005 | Rezai et al. |
| 2005/0187590 A1 | 8/2005 | Boveja et al. |
| 2005/0192644 A1 | 9/2005 | Boveja et al. |
| 2005/0283200 A1 | 12/2005 | Rezai |
| 2006/0009815 A1 | 1/2006 | Boveja |
| 2006/0079936 A1 | 4/2006 | Boveja |
| 2006/0085046 A1 | 4/2006 | Rezai et al. |
| 2006/0100667 A1 | 5/2006 | Machado et al. |
| 2006/0100668 A1* | 5/2006 | Ben-David et al. ............... 607/2 |
| 2011/0046432 A1 | 2/2011 | Simon et al. |
| 2011/0071592 A1 | 3/2011 | Errico et al. |
| 2011/0125203 A1 | 5/2011 | Simon et al. |
| 2011/0125213 A1 | 5/2011 | Simon et al. |
| 2011/0152967 A1 | 6/2011 | Simon et al. |
| 2011/0190569 A1 | 8/2011 | Simon et al. |
| 2011/0230701 A1 | 9/2011 | Simon et al. |
| 2011/0230938 A1 | 9/2011 | Simon et al. |
| 2011/0276107 A1 | 11/2011 | Simon et al. |
| 2011/0276112 A1 | 11/2011 | Simon et al. |
| 2011/0319958 A1 | 12/2011 | Simon et al. |
| 2012/0004701 A1 | 1/2012 | Errico et al. |
| 2012/0029591 A1 | 2/2012 | Simon et al. |
| 2012/0029601 A1 | 2/2012 | Simon et al. |

(56) References Cited

U.S. PATENT DOCUMENTS

OTHER PUBLICATIONS

Sheldon, M.D., Phd., Robert; Role of Pacing in the Treatment of Vasovagal Syncope; The American Journal of Cardiology, vol. 84 (8A); Oct. 21, 1999; pp. 26Q-32Q.

Satish R Raj, M.D. and Robert S. Sheldon, M.D., PHD.; Role of Pacemakers in Treating Neurocardiogenic Syncope; Cardiovascular Research Group, University of Calgary, Alberta, Canada, 2003; pp. 47-52.

Reese S. Terry, W. Brent Tarver and Jacob Zabara; The Implantable Neurocybernetic Prosthesis System; PACE, vol. 14, 1991; pp. 86-93.

Alejandro Valdez-Cruz et al.; Chronic Stimulation of the Cat Vagus Nerve Effect on Sleep and Behavior; Progress in Neuro-Psychopharmacology & Biological Psychiatry 26 (2002); pp. 113-118.

B.A. Malow, M.D., MS; et al.; Vagus Nerve Stimulation Reduces Daytime Sleepiness in Epilepsy Patients; Neurology 57; Sep. (1 of 2) 2001; pp. 879-884.

David Grundy and Tim Scratcherd; Sensory Afferents from the Gastrointestinal Tract; Handbook of Physiology—The Gastrointestinal System; Department of Physiology; University of Sheffield, UK; Chapter 16; pp. 593-619.

Stephen E. Epstein, M.D., et al.; The New England Journal of Medicine; "Treatment of Angina Pectoris by Electrical Stimulation of the Carotid-Sinus Nerves"; vol. 280, May 1, 1960; No. 18; pp. 971-978.

Christopher M. DeGiorgio, et al.; "Vagus Nerve Stimulation: Analysis of Device Parameters in 154 Patients During the Long-Term XE5 Study"; Epilepsia, vol. 42, No. 8, 2001; UCLA Department of Neurology; Revision Accepted Apr. 20, 2001; pp. 1017-1020.

Stuart J. Connolly, M.D., et al.; "Pacemaker Therapy for Prevention of Syncope in Patients with Recurrent Severe Vasovagal Syncope—Second Vasovagal Pacemaker Study (VPS II): A Randomized Trial"; JAMA, May 7, 2003; vol. 289, No. 17; pp. 2224-2229; downloaded from www.jama.com Dec. 5, 2006.

Kevin B. Clark, et al.; "Enhanced Recognition Memory Following Vagus Nerve Stimulation in Human Objects"; Nature Neuroscience, vol. 2, No. 1, Jan. 1, 1999; pp. 94-98.

K. B. Clark, et al.; "Posttraining Electrical Stimulation of Vagal Afferents with Concomitant Vagal Efferent Inactivation Enhances Memory Storage Processes in the Rat"; Neurology of Learning and Memory 70, pp. 364-373 (1998); Article No. NL983863.

Eugene Braunwald, M.D., et al.; "Relief of Angina Pectoris by Electrical Stimulation of the Carotid-Sinus Nerves"; The New England Journal of Medicine, Dec. 1967; vol. 227, No. 24; pp. 1278-1283.

Nina S. Braunwald, M.D., et al.; Carotid Sinus Nerve Stimulation for the Treatment of intractable Angine Pectoris: Surgical Technic; vol. 172; No. 5, Aug. 1969; pp. 870-876.

David S. Bachman, et al.; "Effects of Vagal Volleys and Serotonin on Units of Cingulate Cortex in Monkeys"; Laboratory of Brain Evolution and Behavior, National Institute of Mental Health, Bethesda, MD, 20014; Accepted Nov. 18, 1976; pp. 253-269.

Edited by: Sue Ritter, et al.; Department of Veterinary and Comparative Anatomy, Pharmacology and Physiology College of Veterinary Medicine, Washington State University, Pullman Washington: "Neuroanatomy and Physiology of Abdominal Vagal Afferents"; P.L.R. Andrews and I.N.C. Lawes: Chapter 12: A Protective Role for Vagal Afferents: An Hypothesis; pp. 281-302.

\* cited by examiner

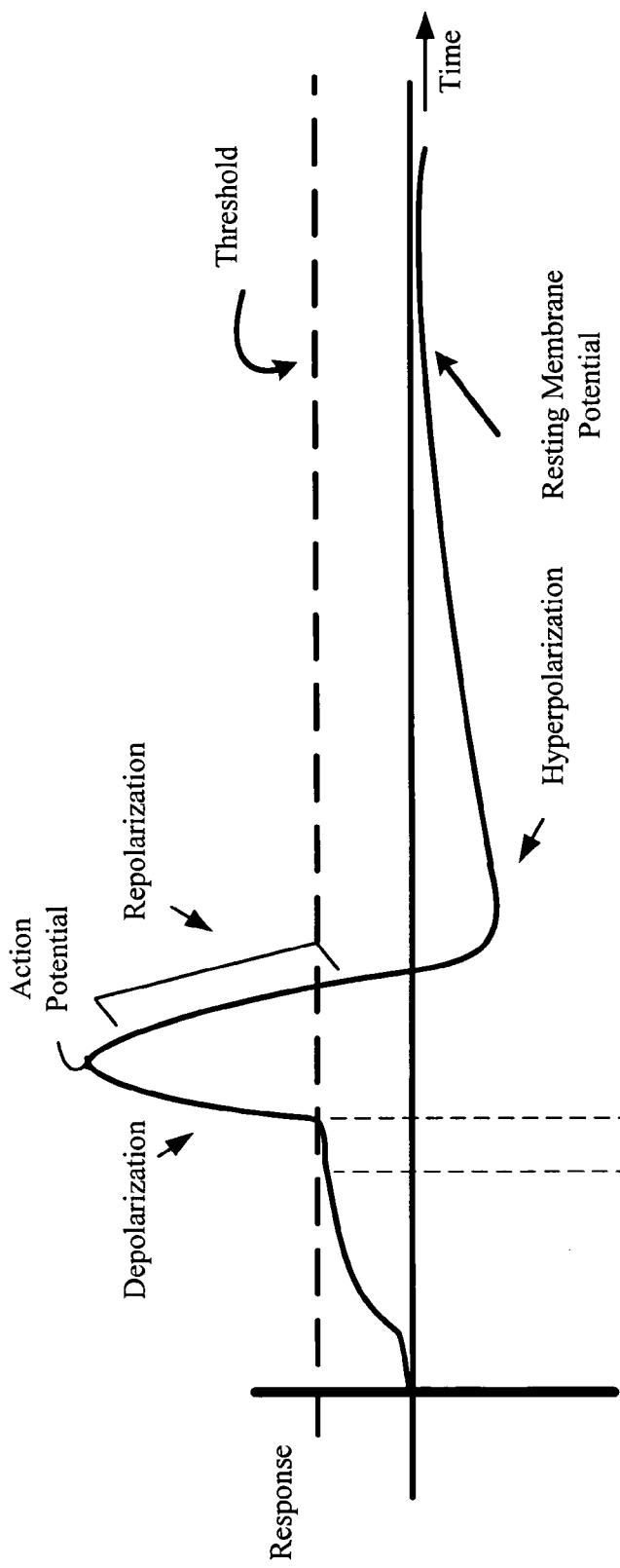
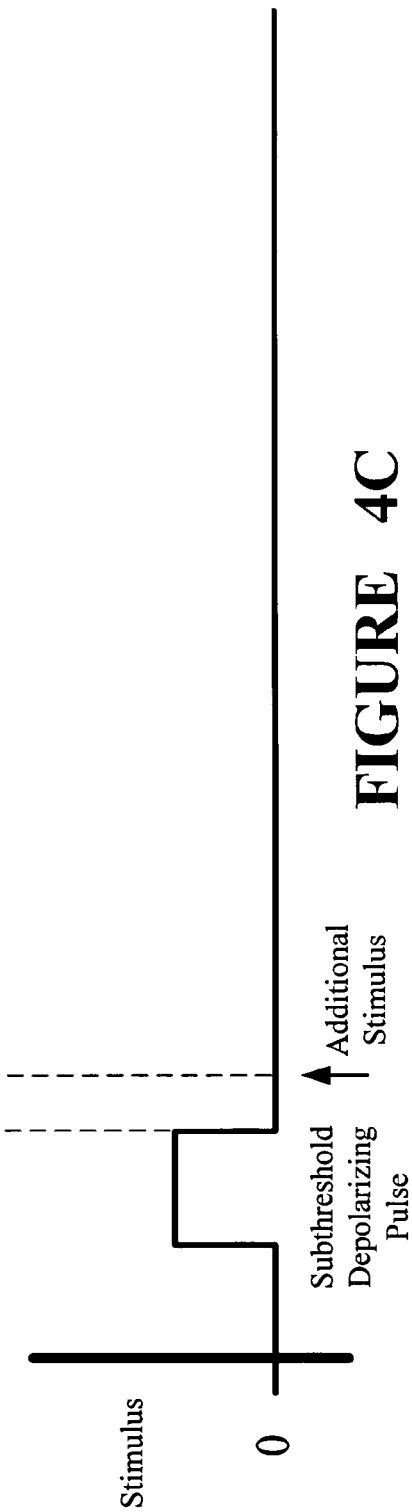
FIGURE 4B
FIGURE 4C

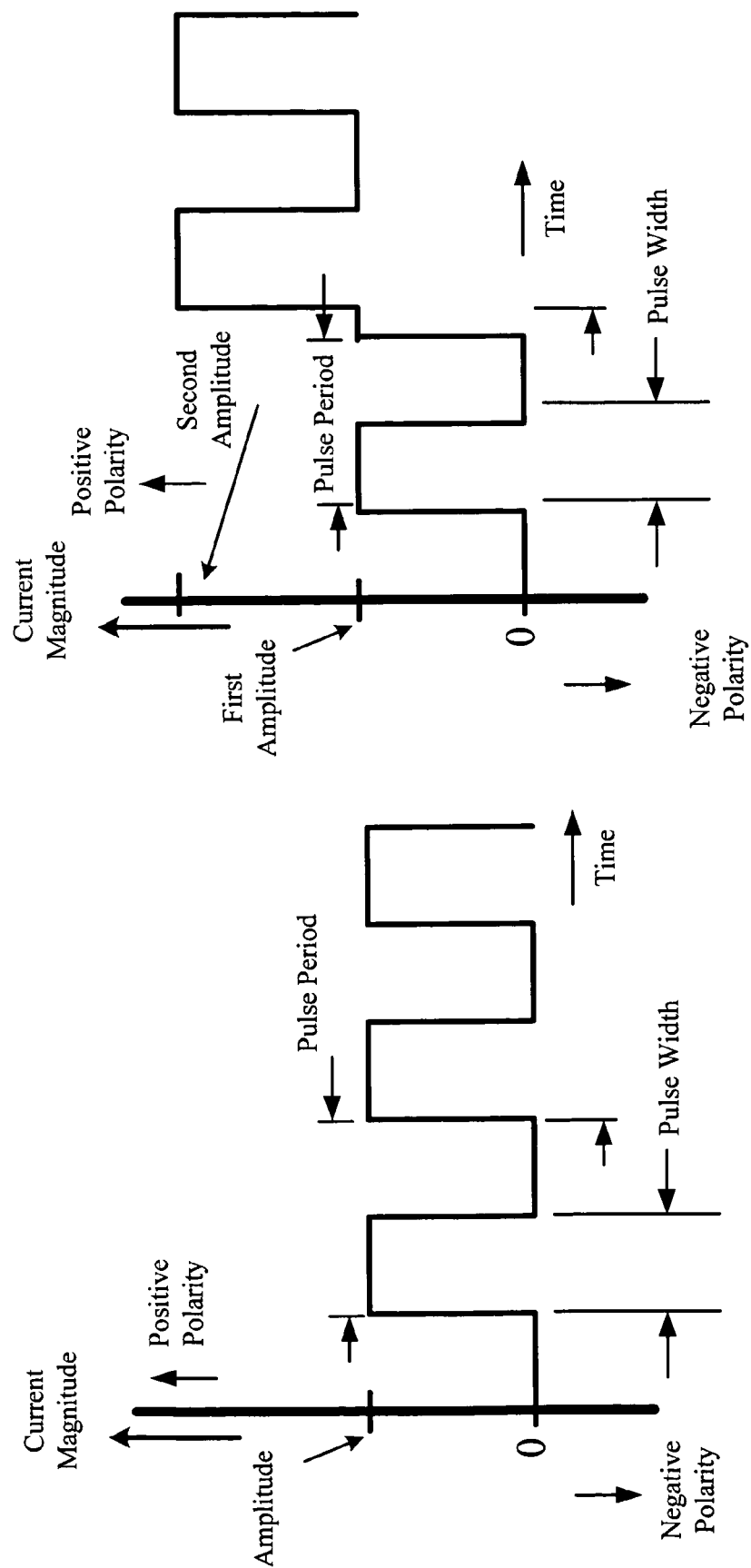

STIMULATING CRANIAL NERVE TO TREAT PULMONARY DISORDER

BACKGROUND OF THE INVENTION

1. Field of the Invention

This invention relates generally to implantable medical devices and, more particularly, to methods, apparatus, and systems for stimulating a cranial nerve of a patient to treat a medical condition, such as pulmonary disorders.

2. Description of the Related Art

The human nervous system (HNS) includes the brain and the spinal cord, collectively known as the central nervous system (CNS). The central nervous system comprises nerve fibers. The network of nerves in the remaining portions of the human body forms the peripheral nervous system (PNS). Some peripheral nerves, known as cranial nerves, connect directly to the brain to control various brain functions, such as vision, eye movement, hearing, facial movement, and feeling. Another system of peripheral nerves, known as the autonomic nervous system (ANS), controls blood vessel diameter, intestinal movements, and actions of many internal organs. Autonomic functions include blood pressure, body temperature, heartbeat and essentially all the unconscious activities that occur without voluntary control.

Like the rest of the human nervous system, nerve signals travel up and down the peripheral nerves, which link the brain to the rest of the human body. Nerve tracts or pathways, in the brain and the peripheral nerves are sheathed in a covering called myelin. The myelin sheath insulates electrical pulses traveling along the nerves. A nerve bundle may comprise up to 100,000 or more individual nerve fibers of different types, including larger diameter A and B fibers which comprise a myelin sheath and C fibers which have a much smaller diameter and are unmyelinated. Different types of nerve fibers, among other things, comprise different sizes, conduction velocities, stimulation thresholds, and myelination status (i.e., myelinated or unmyelinated).

Breathing functions are controlled by various cranial nerves that traverse portions of the human body. For example, the cranial nerve X (i.e., the vagus nerve) traverses down to the region of the lungs of the human body. The vagus nerve traverses down to the chest cavity forming the bronchial branches of the vagus nerve and traverses onto the pulmonary plexus. Breathing operation is controlled by the vagus nerve. The pulmonary plexus refers to the sites of convergence of autonomic fibers which supply the lung. Pulmonary plexus are located proximate the roots of the lungs.

There are various disorders relating to the operation of the lungs. For example, asthma is a chronic lung condition often characterized by difficulty in breathing. Generally, those with asthma tend to have extra-sensitive or hyper-responsive airways. These airways often react by narrowing or obstructing when they become irritated. This irritation causes air flow obstruction, such that movement of air may be restricted in the lungs. This may be exhibited by symptoms such as wheezing, coughing, shortness of breath, and/or chest tightness.

Bronchial constriction is a common result of asthma. Bronchial constriction refers to muscles that encircle the airways when they tighten or go into a spasm. State-of-the-art treatment for asthma generally includes various drugs, oxygen treatment, respiratory treatment, etc. Unfortunately, an asthma attack can occur at unexpected moments due to various reasons, such as allergies. Patients often carry various medication and inhalants to negate the effect of the hyper responsive reaction in the airways of the lungs.

Additionally, other breathing disorders, such as chronic obstructive pulmonary disease, also affect normal operation of the lungs. Chronic obstructive pulmonary disease (COPD) refers to a progressive disease of the airways. COPD may be characterized by a gradual attenuation of lung function. Various disorders that refer to COPD include chronic bronchitis, chronic obstructive bronchitis, emphysema, or a combination of any two or more of these conditions. COPD can be characterized by a substantially disabling shortness of breath. It is estimated that millions of patients suffer from such lung diseases. Lung disorders are often treated by various drugs. One problem associated with the state-of-the-art treatment includes a resistance that may build up to the drugs that are used to treat lung disorders. Additionally, some known drugs are not effective in certain patients. Besides drug regimens or invasive medical procedures, effective treatment for such diseases and disorders are fairly limited.

The present invention is directed to overcoming, or at least reducing, the effects of one or more of the problems set forth above.

SUMMARY OF THE INVENTION

In one aspect, the present invention comprises a method for stimulating a nerve of a patient to treat a pulmonary disorder. At least one electrode is coupled to at least one portion of a vagus nerve of the patient. The portion may include a left vagus nerve and/or a right vagus nerve. An electrical signal is applied to the portion of the vagus nerve using the electrode to treat the pulmonary disorder.

In another aspect, another method for stimulating a portion of a vagus nerve of a patient to treat a pulmonary disorder is provided. At least one electrode is coupled to at least a portion of a vagus nerve of the patient. The portion may include a left vagus nerve and/or a right vagus nerve. An electrical signal generator is provided. The signal generator is coupled to the at least one electrode. An electrical signal is generated using the electrical signal generator. The electrical signal is applied to the electrode to treat the pulmonary disorder. Applying the electrical signal includes blocking an intrinsic neural activity the left vagus nerve or the right vagus nerve. The blocking may be performed using a hyperpolarization or a collision stimulation.

In yet another aspect, another method for stimulating a portion of a vagus nerve of a patient to treat a pulmonary disorder is provided. At least one electrode is coupled to at least a portion of a vagus nerve of the patient. The portion of the vagus nerve may be a left vagus nerve main trunk, a right vagus nerve main trunk, or branch of the vagus nerve of the patient. The branch of the vagus nerve may include a bronchial branch of the vagus nerve or a pulmonary plexus. An electrical signal is applied to the at least one branch of the vagus nerve using the electrode to treat the pulmonary disorder. Applying the electrical signal includes blocking an intrinsic neural activity the left vagus nerve or the right vagus nerve. The blocking may be performed using a hyperpolarization or a collision stimulation.

In yet another aspect, an apparatus for stimulating a portion of a vagus nerve of a patient to treat a pulmonary disorder is provided. The apparatus may include means for coupling at least one electrode to at least one portion of a vagus nerve of the patient. The portion may include a left vagus nerve or a right vagus nerve. The apparatus may also include a means for applying an electrical signal to either of the portion of the vagus nerve using the electrode to treat the pulmonary disorder.

BRIEF DESCRIPTION OF THE DRAWINGS

The invention may be understood by reference to the following description taken in conjunction with the accompanying drawings, in which like reference numerals identify like elements, and in which:

FIG. 4B illustrates an exemplary electrical signal response of a firing neuron as a graph of voltage at a given location at particular times during firing by the neurostimulator of FIG. 2, when applying a sub-threshold depolarizing pulse and additional stimulus to the vagus nerve, in accordance with one illustrative embodiment of the present invention;

FIG. 4C illustrates an exemplary stimulus including a sub-threshold depolarizing pulse and additional stimulus to the vagus nerve for firing a neuron as a graph of voltage at a given location at particular times by the neurostimulator of FIG. 2, in accordance with one illustrative embodiment of the present invention;

FIGS. 5A, 5B, and 5C illustrate exemplary waveforms for generating the electrical signals for stimulating the vagus nerve for treating a pulmonary disorder, according to one illustrative embodiment of the present invention;

Figure 1:
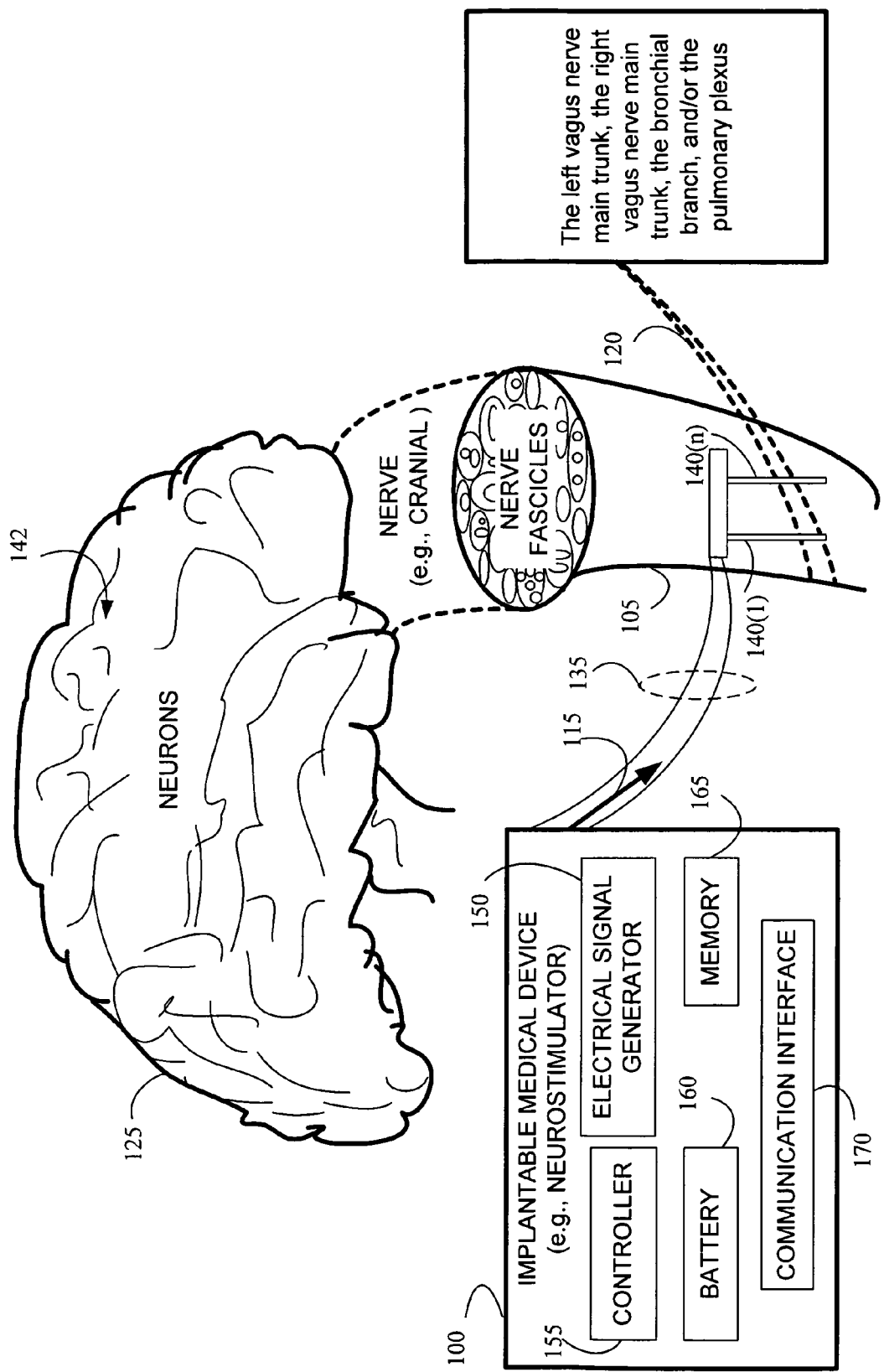
FIG. 1 is a stylized schematic representation of an implantable medical device that stimulates a cranial nerve for treating a patient with a pulmonary disorder, according to one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Certain terms are used throughout the following description and claims refer to particular system components. As one skilled in the art will appreciate, components may be referred to by different names. This document does not intend to distinguish between components that differ in name but not function. In the following discussion and in the claims, the terms "including" and "including" are used in an open-ended fashion, and thus should be interpreted to mean "including, but not limited to." Also, the term "couple" or "couples" is intended to mean either a direct or an indirect electrical connection. For example, if a first device couples to a second device, that connection may be through a direct electrical connection or through an indirect electrical connection via other devices, biological tissues, or magnetic fields. "Direct contact," "direct attachment," or providing a "direct coupling" indicates that a surface of a first element contacts the surface of a second element with no substantial attenuating medium therebetween. The presence of substances, such as bodily fluids, that do not substantially attenuate electrical connections does not vitiate direct contact. The word "or" is used in the inclusive sense (i.e., "and/or") unless a specific use to the contrary is explicitly stated.

Embodiment of the present invention provide for the treatment of pulmonary disorder(s) by stimulation of nerves, such as the vagus nerves.

Cranial nerve stimulation has been used successfully to treat a number of nervous system disorders, including epilepsy and other movement disorders, depression and other neuropsychiatric disorders, dementia, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the recognition that cranial nerve stimulation may be an appropriate treatment for the foregoing conditions, the fact that detailed neural pathways for many (if not all) cranial nerves remain relatively unknown makes predictions of efficacy for any given disorder difficult. Even if such pathways were known, moreover, the precise stimulation parameters that would energize particular pathways that affect the particular disorder likewise are difficult to predict. Accordingly, cranial nerve stimulation, and particularly vagus nerve stimulation, has not heretofore been deemed appropriate for use in treating pulmonary disorders.

In one embodiment of the present invention, methods, apparatus, and systems stimulate a cranial nerve, e.g., a vagus nerve, using an electrical signal to a pulmonary disorder. "Electrical signal" on the nerve refers to the electrical activity (i.e., afferent and/or efferent action potentials) that are not generated by the patient's body and environment, rather applied from, an artificial source, e.g., an implanted neurostimulator. Disclosed herein is a method for treating a pulmonary disorder using stimulation of the vagus nerve (cranial nerve X). A generally suitable form of neurostimulator for use in the method and apparatus of the present invention is disclosed, for example, in U.S. Pat. No. 5,154,172, assigned to the same assignee as the present application. The neurostimulator may be referred to as a NeuroCybernetic Prosthesis (NCP®, Cyberonics, Inc., Houston, Tex., the assignee of the present application). Certain parameters of the electrical stimuli generated by the neurostimulator are programmable, such as be means of an external programmer in a manner conventional for implantable electrical medical devices.

Embodiments of the present invention provide for an electrical stimulation of a portion of a cranial nerve to treat a pulmonary disorder. A portion of the vagus nerve, such as the bronchial branches of the vagus nerve and/or the pulmonary plexus may be stimulated to affect the functions of the pulmonary system of a patient. Stimulation of a portion of the vagus nerve, which is a parasympathetic nerve system, may be used to modify the hyper-responsive reaction of the airways of the lungs of the patient. For example, a controlled electrical stimulation signal, such as a controlled current pulse, may be applied directly and/or in relative proximity of a portion of the vagus nerve, such as the bronchial branches of the vagus nerve. This stimulation may be used to treat various pulmonary disorders, such as asthma, constrictive pulmonary disorder, cardio pulmonary obstructive disorder, etc.

Turning now to FIG. 1, an implantable medical device (IMD) 100 is provided for stimulating a nerve, such as a cranial nerve 105 of a patient to treat a pulmonary disorder using neurostimulation, according to one illustrative embodiment of the present invention. The term "cranial nerve" refers to any portion of the main trunk or any branch of the cranial nerve 105 including cranial nerve fibers, a left cranial nerve and a right cranial nerve. The IMD 100 may deliver an electrical signal 115 to a nerve branch 120 of the cranial nerve 105 that travels to the brain 125 of a patient. The nerve branch 120 provides the electrical signal 115 to the pulmonary system of a patient. The nerve branch 120 may be a nerve branch of the cranial nerve 120 that is associated with the parasympathetic control of the pulmonary function.

The IMD 100 may apply neurostimulation by delivering the electrical signal 115 to the nerve branch 120 via a lead 135 coupled to one or more electrodes 140(1-n). For example, the IMD 100 may stimulate the cranial nerve 105 by applying the electrical signal 115 to the nerve branch 120 that couples to the bronchial branches of the vagus nerve and/or the pulmonary plexus using the electrode(s) 140(1-n).

Consistent with one embodiment of the present invention, the IMD 100 may be a neurostimulator device capable of treating a disease, disorder or condition relating to the pulmonary functions of a patient by providing electrical neurostimulation therapy to a patient. In order to accomplish this task, the IMD 100 may be implanted in the patient at a suitable location. The IMD 100 may apply the electrical signal 115, which may comprise an electrical pulse signal, to the cranial nerve 105. The IMD 100 may generate the electrical signal 115 defined by one or more pulmonary characteristic, such as an asthma condition, a constrictive pulmonary disorder, a cardiac pulmonary obstructive disorder, etc., of the patient. These pulmonary characteristics may be compared to one or more corresponding values within a predetermined range. The IMD 100 may apply the electrical signal 115 to the nerve branch 120 or a nerve fascicle within the cranial nerve 105.

By applying the electrical signal 115, the IMD 100 may treat or control a pulmonary function in a patient.

Implantable medical devices 100 that may be used in the present invention include any of a variety of electrical stimulation devices, such as a neurostimulator capable of stimulating a neural structure in a patient, especially for stimulating a patient's cranial nerve such as a vagus nerve. The IMD 100 is capable of delivering a controlled current stimulation signal. Although the IMD 100 is described in terms of cranial nerve stimulation, and particularly vagus nerve stimulation (VNS), a person of ordinary skill in the art would recognize that the present invention is not so limited. For example, the IMD 100 may be applied to the stimulation of other cranial nerves, such as the trigeminal and/or glossopharyngeal nerves, or other neural tissue, such as one or more brain structures of the patient.

In the generally accepted clinical labeling of cranial nerves, the tenth cranial nerve is the vagus nerve, which originates from the stem of the brain 125. The vagus nerve passes through foramina of the skull to parts of the head, neck and trunk. The vagus nerve branches into left and right branches upon exiting the skull. Left and right vagus nerve branches include both sensory and motor nerve fibers. The cell bodies of vagal sensory nerve fibers are attached to neurons located outside the brain 125 in ganglia groups, and the cell bodies of vagal motor nerve fibers are attached to neurons 142 located within the gray matter of the brain 125. The vagus nerve is a parasympathetic nerve, part of the peripheral nervous system (PNS). Somatic nerve fibers of the cranial nerves are involved in conscious activities and connect the CNS to the skin and skeletal muscles. Autonomic nerve fibers of these nerves are involved in unconscious activities and connect the CNS to the visceral organs such as the heart, lungs, stomach, liver, pancreas, spleen, and intestines. Accordingly, to provide vagus nerve stimulation (VNS), a patient's vagus nerve may be stimulated unilaterally or bilaterally in which a stimulating electrical signal is applied to one or both the branches of the vagus nerve, respectively. For example, coupling the electrodes 140(1-n) comprises coupling an electrode to at least one cranial nerve selected from the group consisting of the left vagus nerve and the right vagus nerve. The term coupling may include actual fixation, proximate location, and the like. The electrodes 140(1-n) may be coupled to a branch of the vagus nerve of the patient. The nerve branch 120 may be selected from the group consisting of a bronchial branch and the pulmonary plexus.

Applying the electrical signal 115 to a selected cranial nerve 105 may comprise generating a response selected from the group consisting of an afferent action potential, an efferent action potential, an afferent hyperpolarization, and an efferent hyperpolarization. The IMD 100 may generate an efferent action potential for treating a pulmonary disorder.

The IMD 100 may comprise an electrical signal generator 150 and a controller 155 operatively coupled thereto to generate the electrical signal 115 for causing the nerve stimulation. The stimulus generator 150 may generate the electrical signal 115. The controller 155 may be adapted to apply the electrical signal 115 to the cranial nerve 105 to provide electrical neurostimulation therapy to the patient for treating a pulmonary disorder. The controller 155 may direct the stimulus generator 150 to generate the electrical signal 115 to stimulate the vagus nerve.

To generate the electrical signal 115, the IMD 100 may further include a battery 160, a memory 165 and a communication interface 170. More specifically, the battery 160 may comprise a power-source battery that may be rechargeable. The battery 160 provides power for the operation of the IMD 100, including electronic operations and the stimulation function. The battery 160, in one embodiment, may be a lithium/thionyl chloride cell or, in another embodiment, a lithium/carbon monofluoride cell. The memory 165, in one embodiment, is capable of storing various data, such as operation parameter data, status data, and the like, as well as program code. The communication interface 170 is capable of providing transmission and reception of electronic signals to and from an external unit. The external unit may be a device that is capable of programming the IMD 100.

The IMD 100, which may be a single device or a pair of devices, is implanted and electrically coupled to the lead(s) 135, which are in turn coupled to the electrode(s) 140 implanted on the left and/or right branches of the vagus nerve, for example. In one embodiment, the electrode(s) 140(1-n) may include a set of stimulating electrode(s) separate from a set of sensing electrode(s). In another embodiment, the same electrode may be deployed to stimulate and to sense. A particular type or a combination of electrodes may be selected as desired for a given application. For example, an electrode suitable for coupling to a vagus nerve may be used. The electrodes 140 may comprise a bipolar stimulating electrode pair. Those skilled in the art having the benefit of the present invention will appreciate that many electrode designs could be used in the present invention.

Using the electrode(s) 140(1-n), the stimulus generator 150 may apply a predetermined sequence of electrical pulses to the selected cranial nerve 105 to provide therapeutic neurostimulation for the patient with a pulmonary disorder. While the selected cranial nerve 105 may be the vagus nerve, the electrode(s) 140(1-n) may comprise at least one nerve electrode for implantation on the patient's vagus nerve for direct stimulation thereof. Alternatively, a nerve electrode may be implanted on or placed proximate to a branch of the patient's vagus nerve for direct stimulation thereof.

A particular embodiment of the IMD 100 may be a programmable electrical signal generator. Such a programmable electrical signal generator may be capable of programmably defining the electrical signal 115. By using at least one parameter selected from the group consisting of a current magnitude, a pulse frequency, and a pulse width, the IMD 100 may treat a pulmonary disorder. The IMD 100 may detect a symptom of the pulmonary disorder. In response to detecting the symptom, the IMD 100 may initiate applying the electrical signal 115. For example, a sensor may be used to detect the symptom of a pulmonary disorder. To treat the pulmonary disorder, the IMD 100 may apply the electrical signal 115 during a first treatment period and further apply a second electrical signal to the cranial nerve 105 using the electrode 140 during a second treatment period.

In one embodiment, the method may further include detecting a symptom of the pulmonary disorder, wherein the applying the electrical signal 115 to the cranial nerve 105 is initiated in response to the detecting of the symptom. In a further embodiment, the detecting the symptom may be performed by the patient. This may involve a subjective observation that the patient is experiencing a symptom of the pulmonary disorder. Alternatively, or in addition, the symptom may be detected by performing a pulmonary disorder test on the patient.

The method may be performed under a single treatment regimen or under multiple treatment regimens. "Treatment regimen" herein may refer to a parameter of the electrical signal 115, a duration for applying the signal, and/or a duty cycle of the signal, among others. In one embodiment, the applying the electrical signal 115 to the cranial nerve 105 is performed during a first treatment period, and may further include the step of applying a second electrical signal to the cranial nerve using the electrode 140 during a second treatment period. In a further embodiment, the method may include detecting a symptom of the pulmonary disorder, wherein the second treatment period is initiated upon the detection of the symptom. The patient may benefit by receiving a first electrical signal during a first, chronic treatment period and a second electrical signal during a second, acute treatment period. Three or more treatment periods may be used, if deemed desirable by a medical practitioner.

Figure 2:
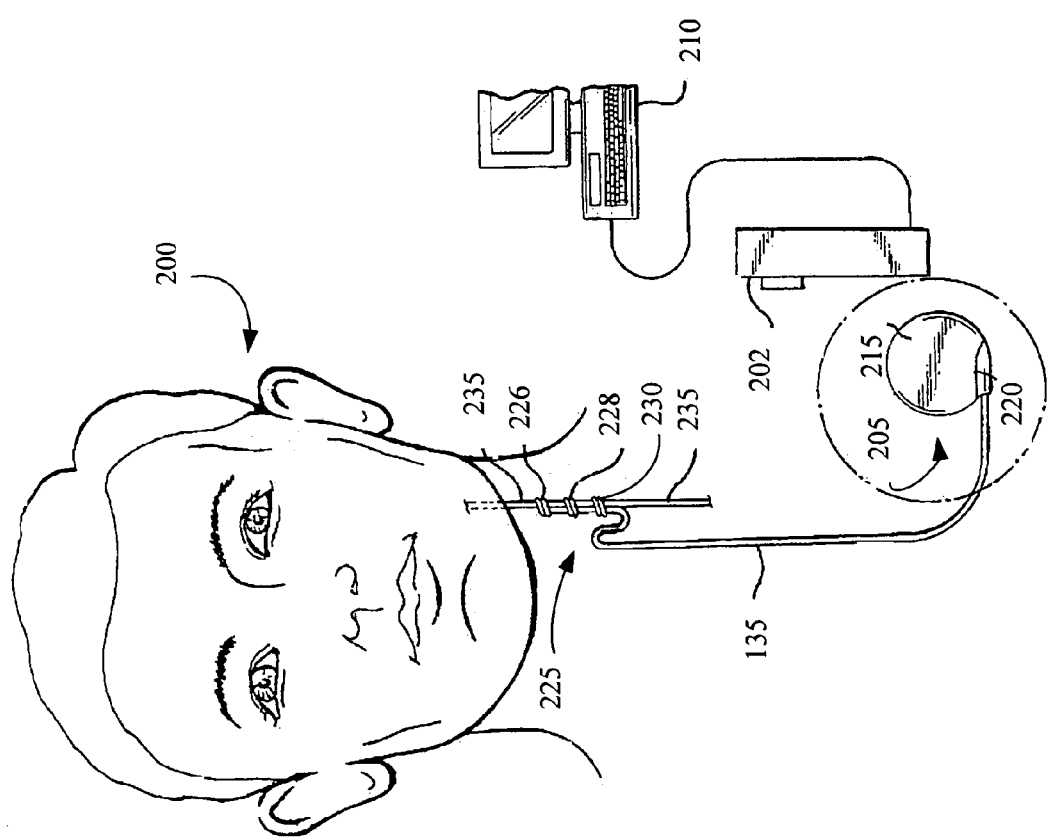
FIG. 2 illustrates one embodiment of a neurostimulator implanted into a patient's body for stimulating the vagus nerve of the patient, with an external programming user interface, in accordance with an illustrative embodiment of the present invention.

A particular embodiment of the IMD 100 shown in FIG. 1 is illustrated in FIG. 2. As shown therein, an electrode assembly 225, which may comprise a plurality of electrodes such as electrodes 226, 228, may be coupled to the cranial nerve 105 such as vagus nerve 235 in accordance with an illustrative embodiment of the present invention. The lead 135 is coupled to the electrode assembly 225 and secured, while retaining the ability to flex with movement of the chest and neck. The lead 135 may be secured by a suture connection to nearby tissue. The electrode assembly 225 may deliver the electrical signal 115 to the cranial nerve 105 to cause desired nerve stimulation for treating a pulmonary disorder. Using the electrode(s) 226, 228, the selected cranial nerve such as vagus nerve 235, may be stimulated within a patient's body 200.

Although FIG. 2 illustrates a system for stimulating the left vagus nerve 235 in the neck (cervical) area, those skilled in the art having the benefit of the present disclosure will understand the electrical signal 105 for nerve stimulation may be applied to the right cervical vagus nerve in addition to, or instead of, the left vagus nerve, and remain within the scope of the present invention. In one such embodiment, lead 135 and electrode 225 assemblies substantially as discussed above may be coupled to the same or a different electrical signal generator.

An external programming user interface 202 may be used by a health professional for a particular patient to either initially program and/or to later reprogram the IMD 100, such as a neurostimulator 205. The neurostimulator 205 may include the electrical signal generator 150, which may be programmable. To enable physician-programming of the electrical and timing parameters of a sequence of electrical impulses, an external programming system 210 may include a processor-based computing device, such as a computer, personal digital assistant (PDA) device, or other suitable computing device.

Using the external programming user interface 202, a user of the external programming system 210 may program the neurostimulator 205. Communications between the neurostimulator 205 and the external programming system 210 may be accomplished using any of a variety of conventional techniques known in the art. The neurostimulator 205 may include a transceiver (such as a coil) that permits signals to be communicated wirelessly between the external programming user interface 202, such as a wand, and the neurostimulator 205.

The neurostimulator 205 having a case 215 with an electrically conducting connector on header 220 may be implanted in the patient's chest in a pocket or cavity formed by the implanting surgeon just below the skin, much as a pacemaker pulse generator would be implanted, for example. A stimulating nerve electrode assembly 225, preferably comprising an electrode pair, is conductively connected to the distal end of an insulated electrically conductive lead assembly 135, which preferably comprises a pair of lead wires and is attached at its proximal end to the connector on the case 215. The electrode assembly 225 is surgically coupled to a vagus nerve 235 in the patient's neck. The electrode assembly 225 preferably comprises a bipolar stimulating electrode pair 226, 228, such as the electrode pair described in U.S. Pat. No. 4,573,481 issued Mar. 4, 1986 to Bullara, which is hereby incorporated by reference herein in its entirety. Persons of skill in the art will appreciate that many electrode designs could be used in the present invention. The two electrodes 226, 228 are preferably wrapped about the vagus nerve, and the electrode assembly 225 secured to the nerve 235 by a spiral anchoring tether 230 such as that disclosed in U.S. Pat. No. 4,979,511 issued Dec. 25, 1990 to Reese S. Terry, Jr. and assigned to the same assignee as the instant application.

In one embodiment, the open helical design of the electrode assembly 225 (described in detail in the above-cited Bullara patent), which is self-sizing and flexible, minimizes mechanical trauma to the nerve and allows body fluid interchange with the nerve. The electrode assembly 225 conforms to the shape of the nerve, providing a low stimulation threshold by allowing a large stimulation contact area. Structurally, the electrode assembly 225 comprises two electrode ribbons (not shown), of a conductive material such as platinum, iridium, platinum-iridium alloys, and/or oxides of the foregoing. The electrode ribbons are individually bonded to an inside surface of an elastomeric body portion of two spiral electrodes, which may comprise two spiral loops of a three-loop helical assembly.

In one embodiment, the lead assembly 230 may comprise two distinct lead wires or a coaxial cable whose two conductive elements are respectively coupled to one of the conductive electrode ribbons. One suitable method of coupling the lead wires or cable to the electrodes comprises a spacer assembly such as that depicted in U.S. Pat. No. 5,531,778 issued Jul. 2, 1996, to Steven Maschino, et al. and assigned to the same Assignee as the instant application, although other known coupling techniques may be used. The elastomeric body portion of each loop is preferably composed of silicone rubber, and the third loop acts as the anchoring tether for the electrode assembly 225.

In one embodiment, the electrode(s) 140(1-n) of IMD 100 (FIG. 1) may sense or detect any target symptom parameter in the patient's body 200. For example, an electrode 140 coupled to the patient's vagus nerve may detect a factor associated with a pulmonary function. The electrode(s) 140 (1-n) may sense or detect a pulmonary disorder condition. For example, a sensor or any other element capable of providing a sensing signal representative of a patient's body parameter associated with activity of the pulmonary functions may be deployed.

In one embodiment, the neurostimulator 205 may be programmed to deliver an electrical biasing signal at programmed time intervals (e.g., every five minutes). In an alternative embodiment, the neurostimulator 205 may be programmed to initiate an electrical biasing signal upon detection of an event or upon another occurrence to deliver therapy. Based on this detection, a programmed therapy may be determined to the patient in response to signal(s) received from one or more sensors indicative of corresponding monitored patient parameters.

The electrode(s) 140(1-n), as shown in FIG. 1 may be used in some embodiments of the invention to trigger administration of the electrical stimulation therapy to the vagus nerve 235 via electrode assembly 225. Use of such sensed body signals to trigger or initiate stimulation therapy is hereinafter referred to as "active," "triggered," or "feedback" modes of administration. Other embodiments of the present invention utilize a continuous, periodic or intermittent stimulus signal. These signals may be applied to the vagus nerve (each of which constitutes a form of continual application of the signal) according to a programmed on/off duty cycle. No sensors may be used to trigger therapy delivery. This type of delivery may be referred to as a "passive," or "prophylactic" therapy mode. Both active and passive electrical biasing signals may be combined or delivered by a single neurostimulator according to the present invention.

The electrical signal generator 150 may be programmed using programming software of the type copyrighted by the assignee of the instant application with the Register of Copyrights, Library of Congress, or other suitable software based on the description herein. A programming wand (not shown) may be used to facilitate radio frequency (RF) communication between the external programming user interface 202 and the electrical signal generator 150. The wand and software permit noninvasive communication with the electrical signal generator 150 after the neurostimulator 205 is implanted. The wand may be powered by internal batteries, and provided with a "power on" light to indicate sufficient power for communication. Another indicator light may be provided to show that data transmission is occurring between the wand and the neurostimulator 205.

The neurostimulator 205 may provide vagus nerve stimulation (VNS) therapy in the upon a vagus nerve branch. The neurostimulator 205 may be activated manually or automatically to deliver the electrical bias signal to the selected cranial nerve via the electrode(s) 226, 228. The neurostimulator 205 may be programmed to deliver the electrical signal 105 continuously, periodically or intermittently when activated.

Figure 3A:
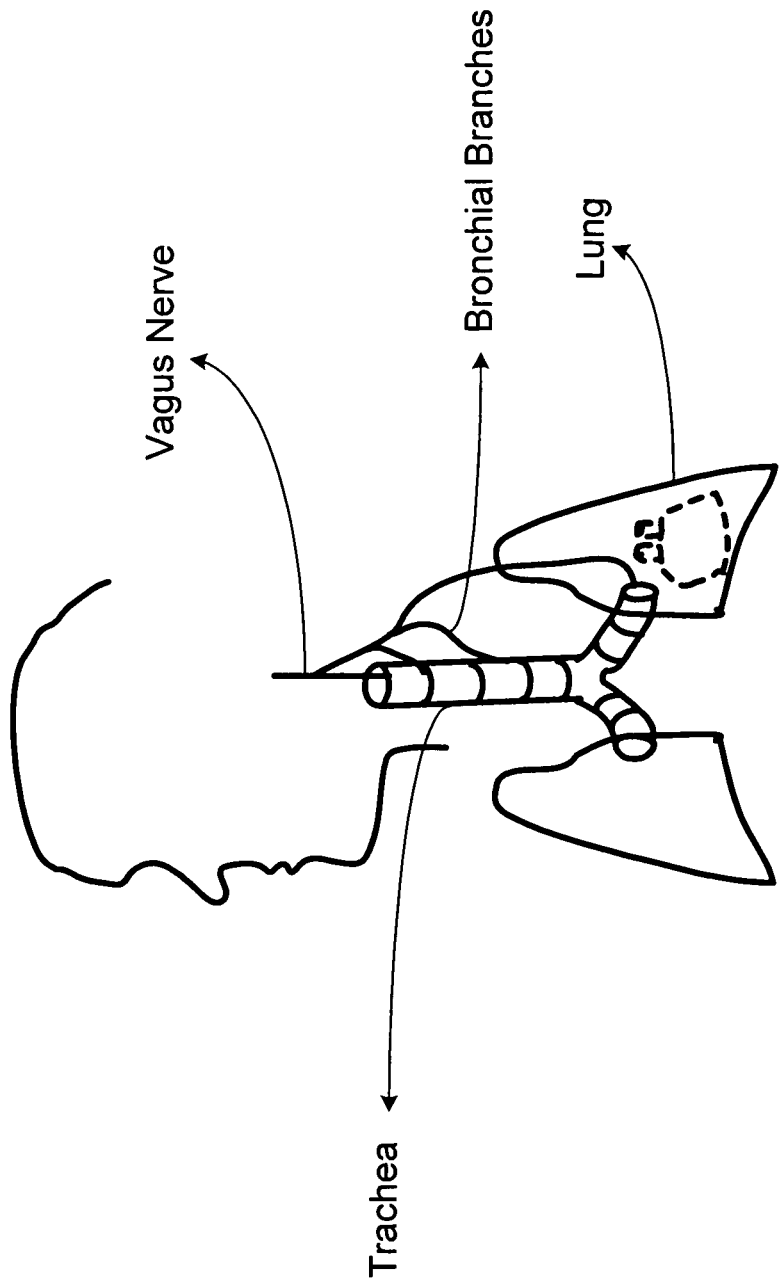
FIG. 3A illustrates a stylized diagram of the lungs, the trachea, the vagus nerve and the bronchial branches.
Figure 3B:
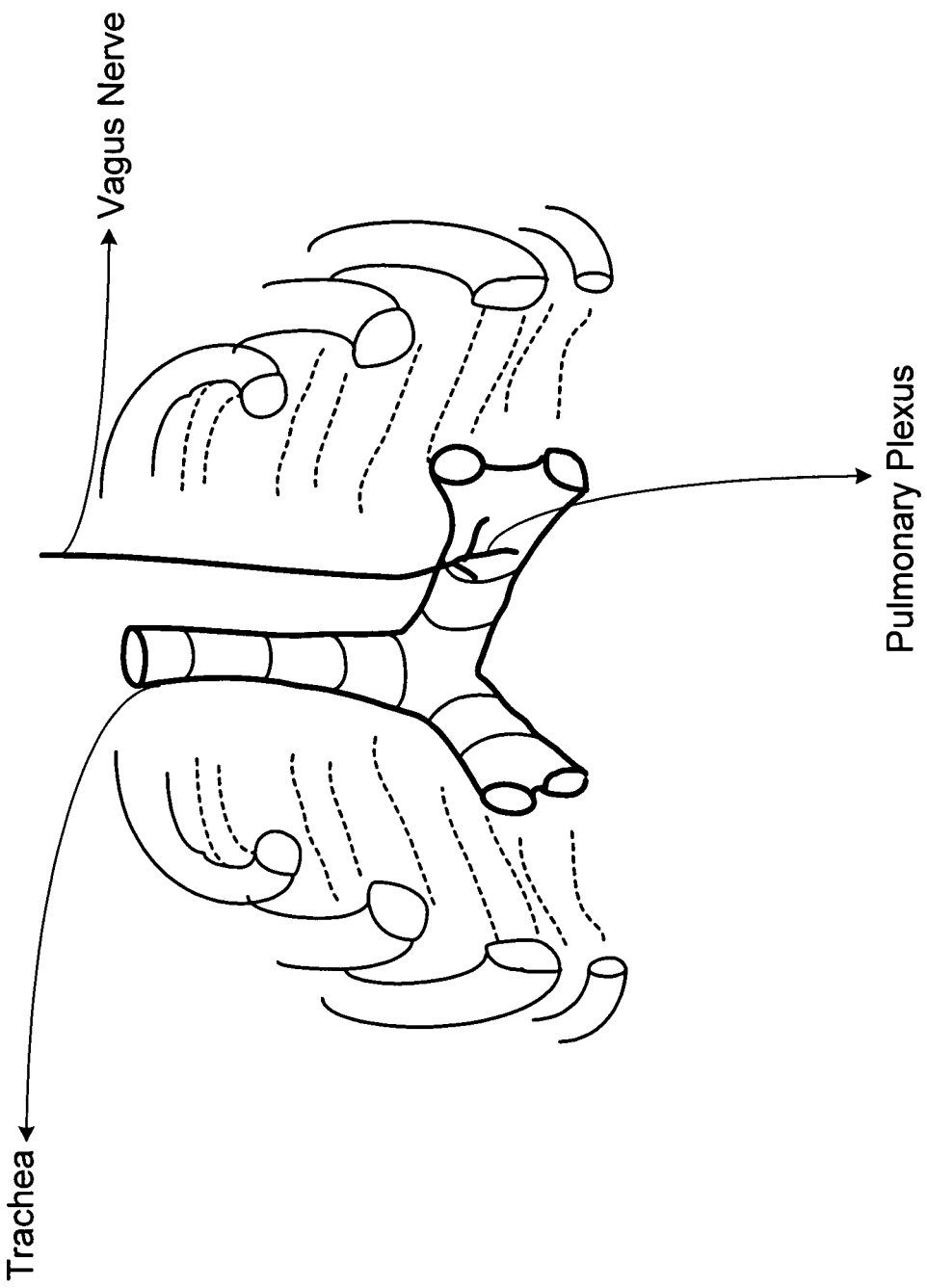
FIG. 3B depicts a stylized diagram of the trachea and the left pulmonary plexus.

Turning now to FIGS. 3A and 3B, a stylized diagram of the lungs, the trachea, the vagus nerve is illustrated. The IMD 100 may be used to stimulate a portion of the vagus nerve, such as a portion of the bronchial branches to treat various disorders, such as asthma, constrictive pulmonary disorder, cardiopulmonary destructive disorder, etc. The diagrams illustrated in FIGS. 3A and 3B have been simplified for ease and clarity of description, however, those skilled in the art would appreciate that various details have been simplified for the sake of clarity.

Referring simultaneously to FIGS. 3A and 3B, the left pulmonary plexus may merge from the bronchial branches of the left vagus nerve. The pulmonary plexus refer to sites of convergence of autonomic fibers that supply the lung. The pulmonary plexus are generally sighted anterior and posterior relative to each lung root. The parasympathetic nerve, which includes the right vagus nerve and the left vagus nerve, may be stimulated to affect the operation of various portions of the pulmonary system of a patient. The pulmonary plexus may provide for parasympathetic and sympathetic stimulation.

The right vagus nerve generally descends posterioinferiorily on the trachea. The right vagus nerve divides posterior to the trachea onto the pulmonary plexus. The pulmonary plexus passes anteriorly to the root of the lung. The left vagus nerve descends anteriorly to the arch of the aorta. The left vagus nerve gives off the recurrent laryngeal branch and then the fibers diverge anteriorly to supply the left pulmonary arterial plexus. Embodiments of the present invention provide for placing an electrode on a portion of the right vagus nerve and/or the left vagus nerve. Additionally, an electrode may be placed in proximity to the pulmonary plexus. Therefore, the electrode(s) become operatively coupled to one or more portions of the vagus nerve and/or to the pulmonary plexus. This way, an electrical signal sent to the electrodes may be directed to affect a reaction in the pulmonary plexus and/or the bronchial branches of the vagus nerve.

In one embodiment, a stimulation may be applied in an efferent manner, which refers to signals being carried away on a nerve from the central nervous system. Therefore, a "blocking" type stimulation signal may be employed using the IMD 100 such that afferent fibers are not stimulated, while efferent fibers are stimulated. The blocking function provided by the stimulation may relate to inhibiting the conduction of action potential by performing hyperpolarization and/or performing collision blocking. Collision blocking may relate to performing high-frequency or rapid stimulation to prevent an action potential in a tissue. The blocking action provides for blocking an intrinsic neural activity on a target portion of a tissue. An appreciable amount of blockage of signals sent back to the brain via the vagus nerve is achieved while employing an efferent type stimulation to affect the operation of portions of the body proximate to the pulmonary plexus and/or the bronchial branches of the vagus nerve. In this way, various disorders may be treated, including asthma, constrictive pulmonary disorder, cardiopulmonary obstructive disorders, etc. For example, by providing efferent stimulation, hyper-responsiveness of the airways may be attenuated in a parasympathetic manner to reduce pulmonary disorders, such as asthma.

In addition to efferent fiber stimulation, additional stimulation may be provided in combination with the blocking type of stimulation described above. Efferent blocking may be realized by enhancing the hyper polarization of a stimulation signal, as described below. Embodiments of the present invention may be employed to cause the IMD 100 to perform stimulation in combination with signal blocking, in order to treat pulmonary disorders. Using stimulation from the IMD 100, parasympathetic nerve portions are be inhibited such that stimulation blocking is achieved, wherein the various portions of the parasympathetic nerve may also be stimulated to affect the pulmonary mechanism in a patient's body. In this way, afferent as well as efferent stimulation may be performed by the IMD 100 to treat various pulmonary disorders.

Figure 4A:
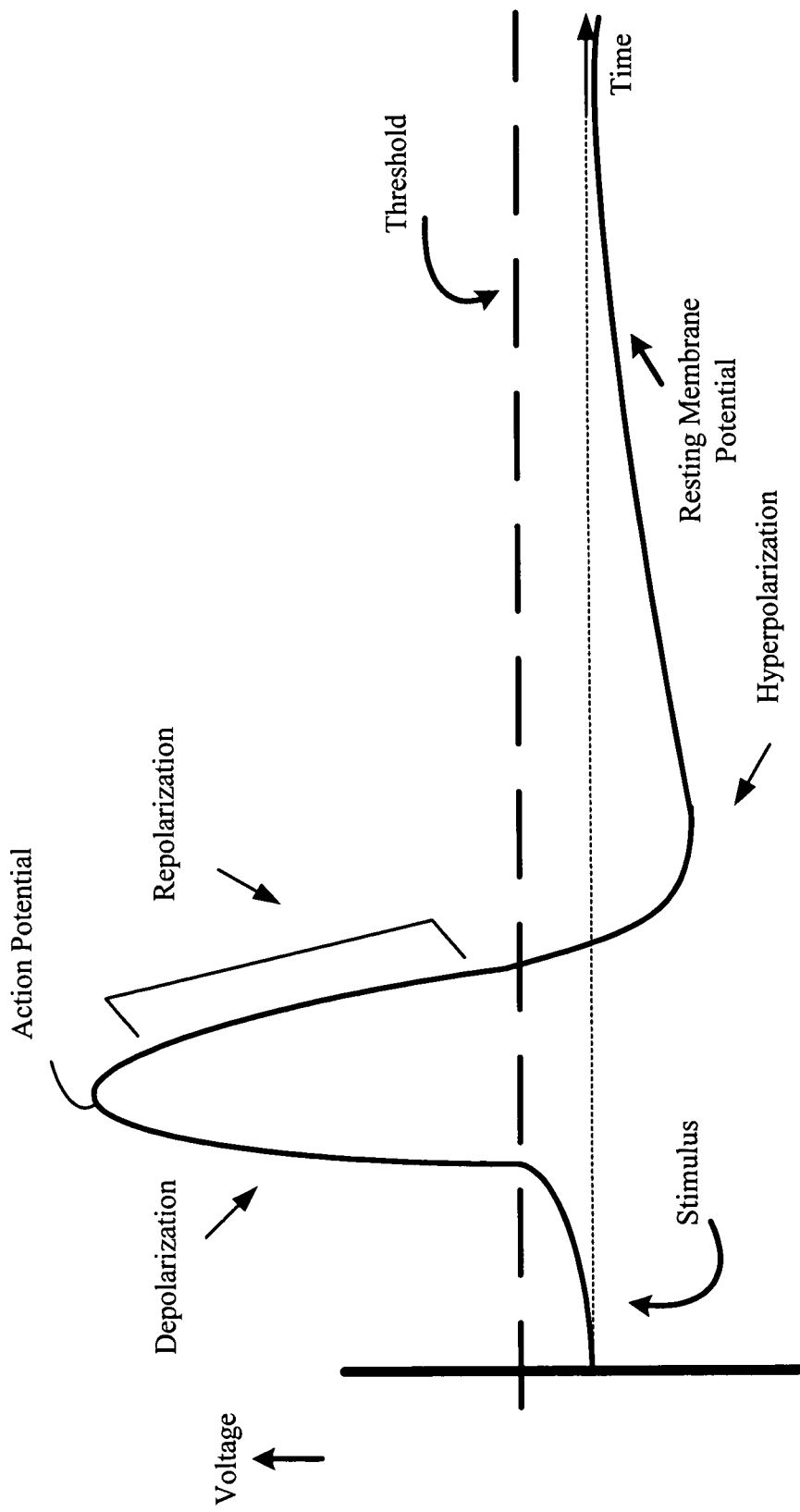
FIG. 4A illustrates an exemplary electrical signal of a firing neuron as a graph of voltage at a given location at particular times during firing by the neurostimulator of FIG. 2, when applying an electrical signal to the vagus nerve, in accordance with one illustrative embodiment of the present invention.

FIG. 4 provides a stylized depiction of an exemplary electrical signal of a firing neuron as a graph of voltage at a given location at particular times during firing, in accordance with one embodiment of the present invention. A typical neuron has a resting membrane potential of about −70 mV, maintained by transmembrane ion channel proteins. When a portion of the neuron reaches a firing threshold of about −55 mV, the ion channel proteins in the locality allow the rapid ingress of extracellular sodium ions, which depolarizes the membrane to about +30 mV. The wave of depolarization then propagates along the neuron. After depolarization at a given location, potassium ion channels open to allow intracellular potassium ions to exit the cell, lowering the membrane potential to about −80 mV (hyperpolarization). About 1 msec is required for transmembrane proteins to return sodium and potassium ions to their starting intra- and extracellular concentrations and allow a subsequent action potential to occur. The present invention may raise or lower the resting membrane potential, thus making the reaching of the firing threshold more or less likely and subsequently increasing or decreasing the rate of fire of any particular neuron.

Referring to FIG. 4B, an exemplary electrical signal response is illustrated of a firing neuron as a graph of voltage at a given location at particular times during firing by the neurostimulator of FIG. 2, in accordance with one illustrative embodiment of the present invention. As shown in FIG. 4C, an exemplary stimulus including a sub-threshold depolarizing pulse and additional stimulus to the cranial nerve 105, such as the vagus nerve 235 may be applied for firing a neuron, in accordance with one illustrative embodiment of the present invention. The stimulus illustrated in FIG. 4C depicts a graph of voltage at a given location at particular times by the neurostimulator of FIG. 2.

The neurostimulator may apply the stimulus voltage of FIG. 4C to the cranial nerve 105, which may include afferent fibers, efferent fibers, or both. This stimulus voltage may cause the response voltage shown in FIG. 4B. Afferent fibers transmit information to the brain from the extremities; efferent fibers transmit information from the brain to the extremities. The vagus nerve 235 may include both afferent and efferent fibers, and the neurostimulator 205 may be used to stimulate either or both.

The cranial nerve 105 may include fibers that transmit information in the sympathetic nervous system, the parasympathetic nervous system, or both. Inducing an action potential in the sympathetic nervous system may yield a result similar to that produced by blocking an action potential in the parasympathetic nervous system and vice versa.

Figure 5C:
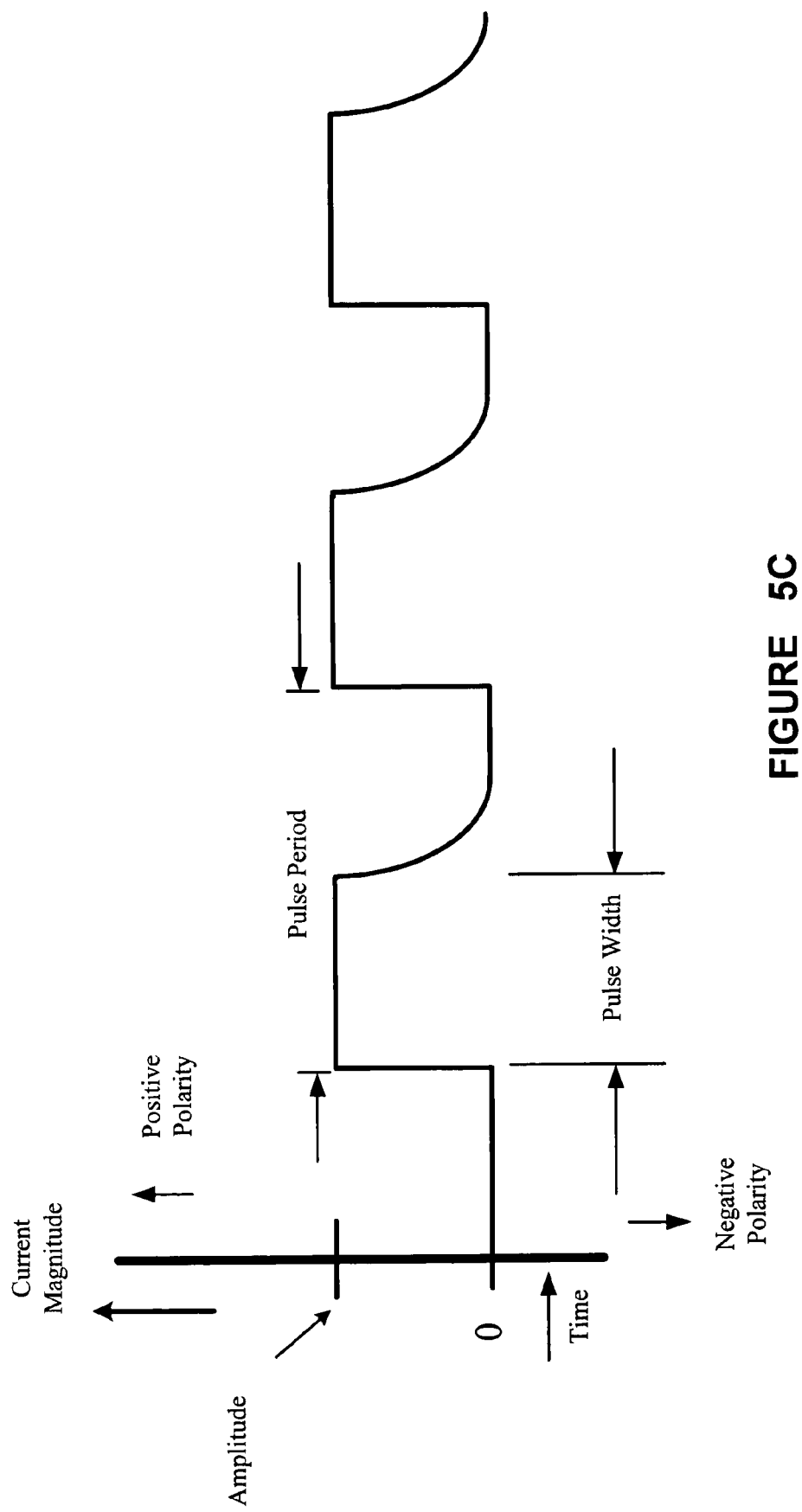

Returning back to FIG. 2, the neurostimulator 205 may generate the electrical signal 115 according to one or more programmed parameters for stimulation of the vagus nerve 235. In one embodiment, the stimulation parameter may be selected from the group consisting of a current magnitude, a pulse frequency, a signal width, on-time, and off-time. An exemplary table of ranges for each of these stimulation parameters is provided in Table 1. The stimulation parameter may be of any suitable waveform; exemplary waveforms in accordance with one embodiment of the present invention are shown in FIGS. 5A-5C. Specifically, the exemplary waveforms illustrated in FIGS. 5A-5C depict the generation of the electrical signal 115 that may be defined by a factor related to at least one of an asthma condition, constrictive pulmonary disorder, and a cardiac pulmonary obstructive disorder of the patient relative to a value within a defined range.

According to one illustrative embodiment of the present invention, various electrical signal patterns may be employed by the neurostimulator 205. These electrical signals may include a plurality of types of pulses, e.g., pulses with varying amplitudes, polarity, frequency, etc. For example, the exemplary waveform 5A depicts that the electrical signal 115 may be defined by fixed amplitude, constant polarity, pulse width, and pulse period. The exemplary waveform 5B depicts that the electrical signal 115 may be defined by a variable amplitude, constant polarity, pulse width, and pulse period. The exemplary waveform 5C depicts that the electrical signal 115 may be defined by a fixed amplitude pulse with a relatively slowly discharging current magnitude, constant polarity, pulse width, and pulse period. Other types of signals may also be used, such as sinusoidal waveforms, etc. The electrical signal may be controlled current signals.

TABLE 1

| PARAMETER | RANGE |
| --- | --- |
| Output current | 0.1-6.0 mA |
| Pulse width | 10-1500 μsec |
| Frequency | 0.5-250 Hz |
| On-time | 1 sec and greater |
| Off-time | 0 sec and greater |
| Frequency Sweep | 10-100 Hz |
| Random Frequency | 10-100 Hz |

On-time and off-time parameters may be used to define an intermittent pattern in which a repeating series of signals may be generated for stimulating the nerve 105 during the on-time. Such a sequence may be referred to as a "pulse burst." This sequence may be followed by a period in which no signals are generated. During this period, the nerve is allowed to recover from the stimulation during the pulse burst. The on/off duty cycle of these alternating periods of stimulation and idle periods may have a ratio in which the off-time may be set to zero, providing continuous stimulation. Alternatively, the idle time may be as long as one day or more, in which case the stimulation is provided once per day or at even longer intervals. Typically, however, the ratio of "off-time" to "on-time" may range from about 0.5 to about 10.

In one embodiment, the width of each signal may be set to a value not greater than about 1 msec, such as about 250-500 μsec, and the signal repetition frequency may be programmed to be in a range of about 20-250 Hz. In one embodiment, a frequency of 150 Hz may be used. A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

In one embodiment, the present invention may include coupling of at least one electrode to each of two or more cranial nerves. (In this context, two or more cranial nerves means two or more nerves having different names or numerical designations, and do not refer to the left and right versions of a particular nerve). In one embodiment, at least one electrode 140 may be coupled to each of the vagus nerve 235 and/or a branch of the vagus nerve. The electrode may be operatively coupled to the bronchial branch of the vagus nerve and/or to the pulmonary plexus. The term "operatively" coupled may include directly or indirectly coupling. Each of the nerves in this embodiment or others involving two or more cranial nerves may be stimulated according to particular activation modalities that may be independent between the two nerves.

Another activation modality for stimulation is to program the output of the neurostimulator 205 to the maximum amplitude which the patient may tolerate. The stimulation may be cycled on and off for a predetermined period of time followed by a relatively long interval without stimulation. Where the cranial nerve stimulation system is completely external to the patient's body, higher current amplitudes may be needed to overcome the attenuation resulting from the absence of direct contact with the vagus nerve 235 and the additional impedance of the skin of the patient. Although external systems typically require greater power consumption than implantable ones, they have an advantage in that their batteries may be replaced without surgery.

Other types of indirect stimulations may be performed in conjunction with embodiments of the invention. In one embodiment, the invention includes providing noninvasive transcranial magnetic stimulation (TMS) to the brain 125 of the patient along with the IMD 100 of the present information to treat the pulmonary disorder. TMS systems include those disclosed in U.S. Pat. Nos. 5,769,778; 6,132,361; and 6,425,852. Where TMS is used, it may be used in conjunction with cranial nerve stimulation as an adjunctive therapy. In one embodiment, both TMS and direct cranial nerve stimulation may be performed to treat the pulmonary disorder. Other types of stimulation, such as chemical stimulation to treat pulmonary disorders may be performed in combination with the IMD 100.

Returning to systems for providing direct cranial nerve stimulation, such as that shown in FIGS. 1 and 2, stimulation may be provided in at least two different modalities. Where cranial nerve stimulation is provided based solely on programmed off-times and on-times, the stimulation may be referred to as passive, inactive, or non-feedback stimulation. In contrast, stimulation may be triggered by one or more feedback loops according to changes in the body or mind of the patient. This stimulation may be referred to as active or feedback-loop stimulation. In one embodiment, feedback-loop stimulation may be manually-triggered stimulation, in which the patient manually causes the activation of a pulse burst outside of the programmed on-time/off-time cycle. The patient may manually activate the neurostimulator 205 to stimulate the cranial nerve 105 to treat the acute episode of a pulmonary disorder, such as an asthma attack. The patient may also be permitted to alter the intensity of the signals applied to the cranial nerve within limits established by the physician. For example, the patient may be permitted to alter the signal frequency, current, duty cycle, or a combination thereof. In at least some embodiments, the neurostimulator 205 may be programmed to generate the stimulus for a relatively long period of time in response to manual activation.

Patient activation of a neurostimulator 205 may involve use of an external control magnet for operating a reed switch in an implanted device, for example. Certain other techniques of manual and automatic activation of implantable medical devices are disclosed in U.S. Pat. No. 5,304,206 to Baker, Jr., et al., assigned to the same assignee as the present application ("the '206 patent"). According to the '206 patent, means for manually activating or deactivating the electrical signal generator 150 may include a sensor such as piezoelectric element mounted to the inner surface of the generator case and adapted to detect light taps by the patient on the implant site. One or more taps applied in fast sequence to the skin above the location of the electrical signal generator 150 in the patient's body 200 may be programmed into the implanted medical device 100 as a signal for activation of the electrical signal generator 150. Two taps spaced apart by a slightly longer duration of time may be programmed into the IMD 100 to indicate a desire to deactivate the electrical signal generator 150, for example. The patient may be given limited control over operation of the device to an extent which may be determined by the program dictated or entered by the attending physician. The patient may also activate the neurostimulator 205 using other suitable techniques or apparatus.

In some embodiments, feedback stimulation systems other than manually-initiated stimulation may be used in the present invention. A cranial nerve stimulation system may include a sensing lead coupled at its proximal end to a header along with a stimulation lead and electrode assemblies. A sensor may be coupled to the distal end of the sensing lead. The sensor may include a temperature sensor, a breathing parameter sensor, a heart parameter sensor, a brain parameter sensor, or a sensor for another body parameter. The sensor may also include a nerve sensor for sensing activity on a nerve, such as a cranial nerve, such as the vagus nerve 235.

In one embodiment, the sensor may sense a body parameter that corresponds to a symptom of pulmonary disorder. If the sensor is to be used to detect a symptom of the medical disorder, a signal analysis circuit may be incorporated into the neurostimulator 205 for processing and analyzing signals from the sensor. Upon detection of the symptom of the pulmonary disorder, the processed digital signal may be supplied to a microprocessor in the neurostimulator 205 to trigger application of the electrical signal 115 to the cranial nerve 105. In another embodiment, the detection of a symptom of interest may trigger a stimulation program including different stimulation parameters from a passive stimulation program. This may entail providing a higher current stimulation signal or providing a higher ratio of on-time to off-time.

In response to the afferent action potentials, the detection communicator may detect an indication of change in the symptom characteristic. The detection communicator may provide feedback for the indication of change in the symptom characteristic to modulate the electrical signal 115. In response to providing feedback for the indication, the electrical signal generator 150 may adjust the afferent action potentials to enhance efficacy of a drug in the patient.

The neurostimulator 205 may use the memory 165 to store disorder data and a routine to analyze this data. The disorder data may include sensed body parameters or signals indicative of the sensed parameters. The routine may comprise software and/or firmware instructions to analyze the sensed hormonal activity for determining whether electrical neurostimulation would be desirable. If the routine determines that electrical neurostimulation is desired, then the neurostimulator 205 may provide an appropriate electrical signal to a neural structure, such as the vagus nerve 235.

In certain embodiments, the IMD 100 may comprise a neurostimulator 205 having a case 215 as a main body in which the electronics described in FIGS. 1-2 may be enclosed and hermetically sealed. Coupled to the main body may be the header 220 designed with terminal connectors for connecting to a proximal end of the electrically conductive lead(s) 135. The main body may comprise a titanium shell, and the header may comprise a clear acrylic or other hard, biocompatible polymer such as polycarbonate, or any material that may be implantable into a human body. The lead(s) 135 projecting from the electrically conductive lead assembly 230 of the header may be coupled at a distal end to electrodes 140(1-n). The electrodes 140(1-n) may be coupled to neural structure such as the vagus nerve 235, utilizing a variety of methods for operatively coupling the lead(s) 135 to the tissue of the vagus nerve 235. Therefore, the current flow may take place from one terminal of the lead 135 to an electrode such as electrode 226 (FIG. 2) through the tissue proximal to the vagus nerve 235, to a second electrode such as electrode 228 and a second terminal of the lead 135.

Figure 6:
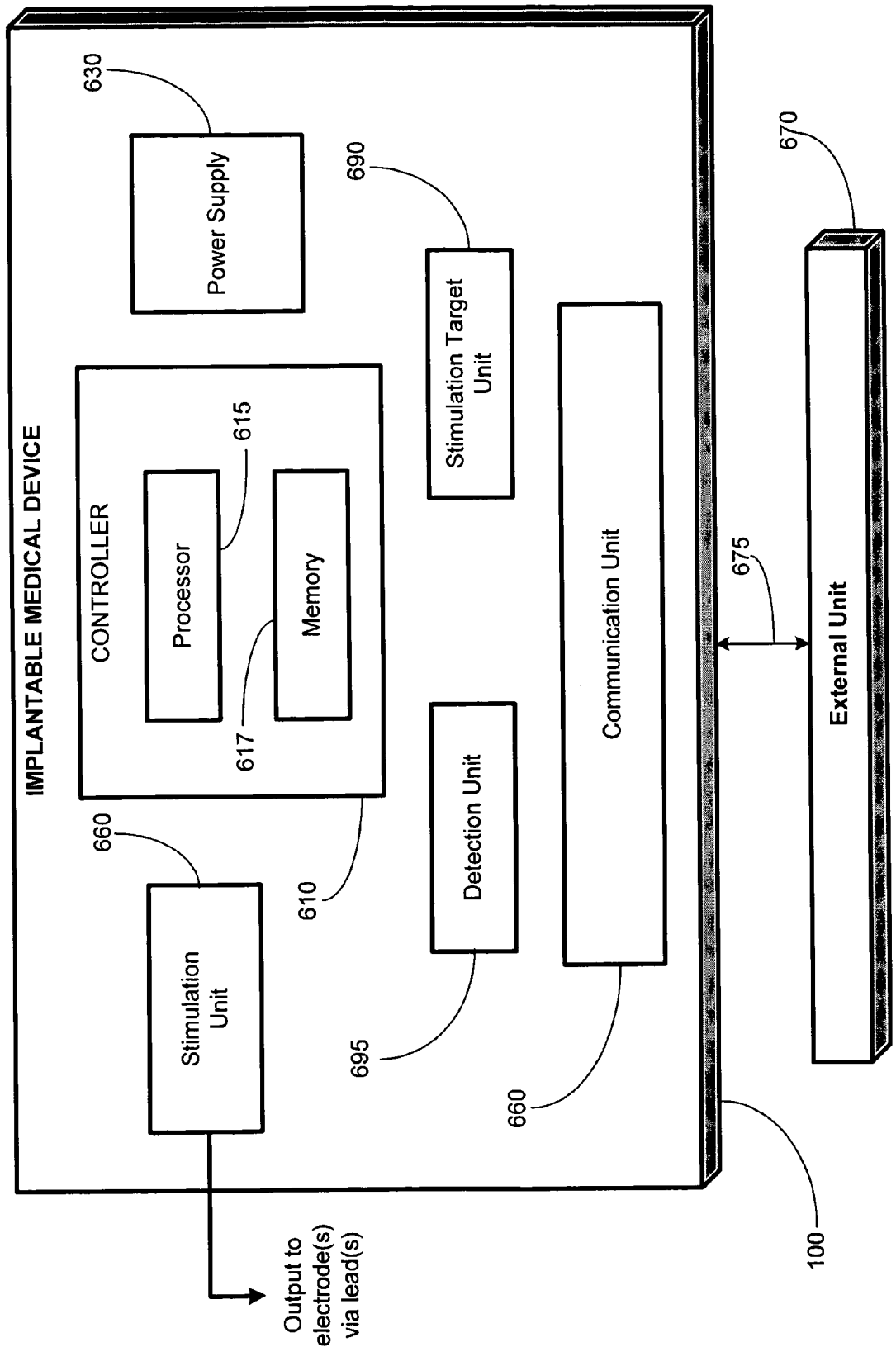
FIG. 6 illustrates a stylized block diagram depiction of the implantable medical device for treating a pulmonary disorder, in accordance with one illustrative embodiment of the present invention.

Turning now to FIG. 6, a block diagram depiction of the IMD 100, in accordance with an illustrative embodiment of the present invention is provided. The IMD 100 may comprise a controller 610 capable of controlling various aspects of the operation of the IMD 100. The controller 610 is capable of receiving internal data and/or external data and generating and delivering a stimulation signal to target tissues of the patient's body. For example, the controller 610 may receive manual instructions from an operator externally, or may perform stimulation based on internal calculations and programming. The controller 610 is capable of affecting substantially all functions of the IMD 100.

The controller 610 may comprise various components, such as a processor 615, a memory 617, etc. The processor 615 may comprise one or more microcontrollers, microprocessors, etc., that are capable of performing various executions of software components. The memory 617 may comprise various memory portions where a number of types of data (e.g., internal data, external data instructions, software codes, status data, diagnostic data, etc.) may be stored. The memory 617 may comprise random access memory (RAM) dynamic random access memory (DRAM), electrically erasable programmable read-only memory (EEPROM), flash memory, etc.

The IMD 100 may also comprise a stimulation unit 620. The stimulation unit 620 is capable of generating and delivering stimulation signals to one or more electrodes via leads. A number of leads 122, 134, 137 may be coupled to the IMD 100. Therapy may be delivered to the leads 122 by the stimulation unit 620 based upon instructions from the controller 610. The stimulation unit 620 may comprise various circuitry, such as stimulation signal generators, impedance control circuitry to control the impedance "seen" by the leads, and other circuitry that receives instructions relating to the type of stimulation to be performed. The stimulation unit 620 is capable of delivering a controlled current stimulation signal over the leads 122.

The IMD 100 may also comprise a power supply 630. The power supply 630 may comprise a battery, voltage regulators, capacitors, etc., to provide power for the operation of the IMD 100, including delivering the stimulation signal. The power supply 630 comprises a power-source battery that in some embodiments may be rechargeable. In other embodiments, a non-rechargeable battery may be used. The power supply 630 provides power for the operation of the IMD 100, including electronic operations and the stimulation function. The power supply 630, may comprise a lithium/thionyl chloride cell or a lithium/carbon monofluoride cell. Other battery types known in the art of implantable medical devices may also be used.

The IMD 100 also comprises a communication unit 660 capable of facilitating communications between the IMD 100 and various devices. In particular, the communication unit 660 is capable of providing transmission and reception of electronic signals to and from an external unit 670. The external unit 670 may be a device that is capable of programming various modules and stimulation parameters of the IMD 100. In one embodiment, the external unit 670 is a computer system that is capable of executing a data-acquisition program. The external unit 670 may be controlled by a healthcare provider, such as a physician, at a base station in, for example, a doctor's office. The external unit 670 may be a computer, preferably a handheld computer or PDA, but may alternatively comprise any other device that is capable of electronic communications and programming. The external unit 670 may download various parameters and program software into the IMD 100 for programming the operation of the implantable device. The external unit 670 may also receive and upload various status conditions and other data from the IMD 100. The communication unit 660 may be hardware, software, firmware, and/or any combination thereof. Communications between the external unit 670 and the communication unit 660 may occur via a wireless or other type of communication, illustrated generally by line 675 in FIG. 6.

The IMD 100 also comprises a detection unit 695, which is capable of detecting various conditions and characteristics of the pulmonary functions of a patient. For example, the detection unit 695 may comprise hardware, software, or firmware that is capable of determining a respiratory rate, a heart rate, a pulse oxygen level, an oxygen saturation factor in the blood, a carbon dioxide factor in the blood, and the like. The detection unit 695 may comprise means for deciphering data from various sensors that are capable of measuring respiratory rates, heart rate, RSA, pulse oxygen, etc. Additionally, the detection unit 695 may decipher data from external sources, wherein data from the external device 670 may be provided to the IMD 100. External inputs may include data such as results from breathing testing, external pulse oxygen measurements, heart rate monitors, respiratory rate monitors, etc. The detection unit 695 may also detect an input from the patient or an operator indicating that an onset of breathing difficulty, such as an asthma attack. Based upon data deciphered by the detection unit 695, the IMD 100 may deliver stimulation to a portion of the vagus nerve to affect the pulmonary functions in the patient.

The IMD 100 may also comprise a stimulation target unit 690 that is capable of directing a stimulation signal to one or more electrodes that is proximate to the various portions of the vagus nerve, such as the left pulmonary plexus and/or the bronchial branches of the vagus nerve. In this way, the stimulation target unit 690 is capable of targeting a predetermined portion of the pulmonary region, such as the left pulmonary plexus. Therefore, for a particular type of data detected by the detection unit 695, the stimulation target unit 690 may stimulate a selected portion of the pulmonary system to perform an afferent, efferent, and/or an afferent in combination with an efferent stimulation, to treat a breathing disorder. Therefore, upon an onset of an asthma attack, for example, the IMD 100 may select various portions of the vagus nerve, specifically the bronchial branches, or a portion of the pulmonary plexus to stimulate to perform an efferent and/or an afferent-efferent combination stimulation, in order to alleviate the asthma attack.

One or more blocks illustrated in the block diagram of IMD 100 in FIG. 6 may comprise hardware units, software units, firmware units and/or any combination thereof. Additionally, one or more blocks illustrated in FIG. 6 may be combined with other blocks, which may represent circuit hardware units, software algorithms, etc. Additionally, any number of the circuitry or software units associated with the various blocks illustrated in FIG. 6 may be combined into a programmable device, such as a field programmable gate array, an ASIC device, etc.

Figure 7:
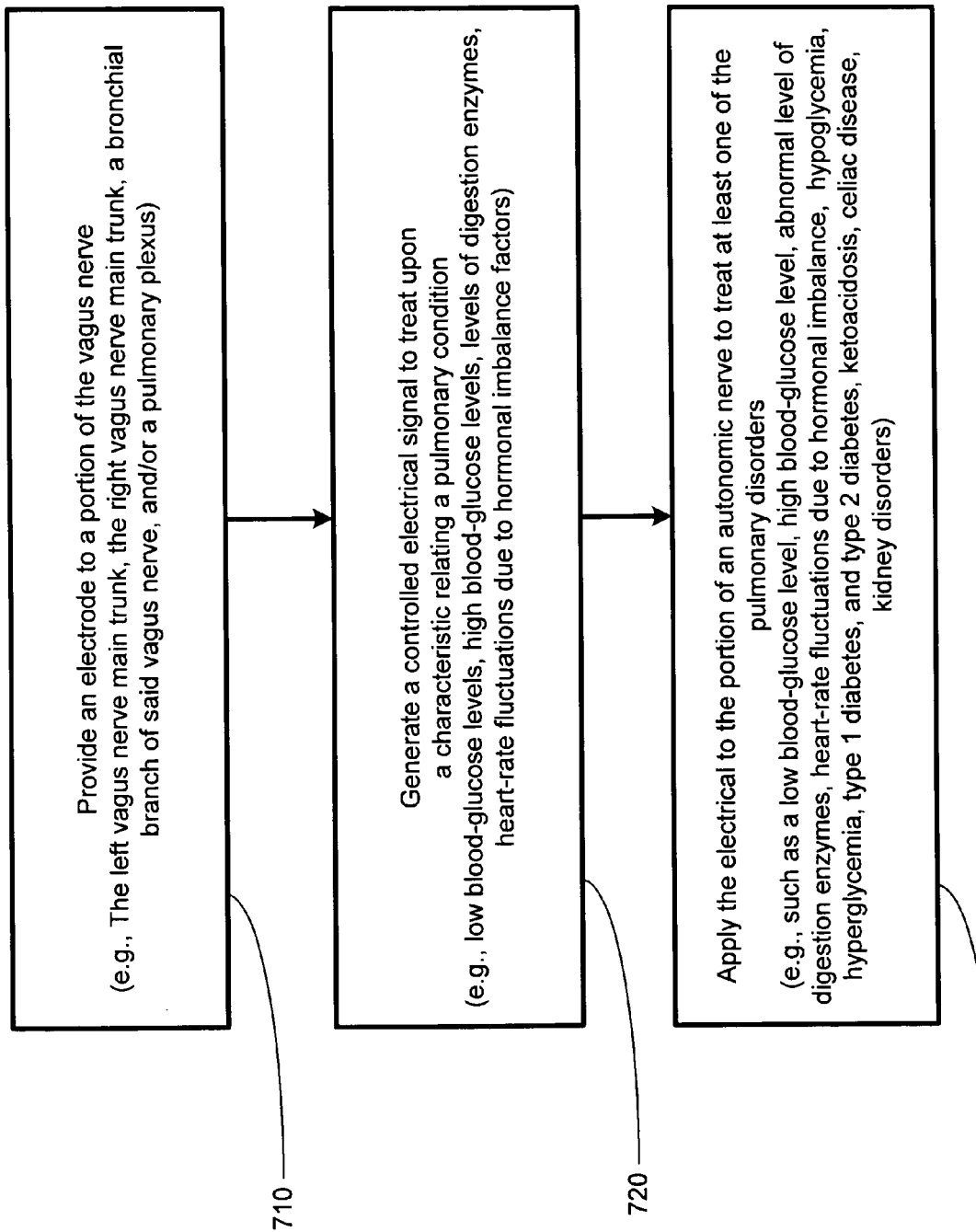
FIG. 7 illustrates a flowchart depiction of a method for treating a pulmonary disease, in accordance with illustrative embodiment of the present invention.

Turning now to FIG. 7, a flowchart depiction of a method for treating a pulmonary disorder, in accordance with one illustrative embodiment of the present invention is provided. An electrode may be coupled to a portion of a vagus nerve to perform a stimulation and/or a blocking function to treat a breathing disorder. In one embodiment, a plurality of electrodes may be positioned in electrical contact or proximate to a portion of the vagus nerve to deliver a stimulation to the portion of the vagus nerve (block 710). The IMD 100 may then generate a controlled electrical signal, based upon one or more characteristic relating to the breathing condition of the patient (block 720). This may include a predetermined electrical signal that is preprogrammed based upon a particular condition of a patient, such as an asthma condition, a constrictive pulmonary disorder condition, a cardiopulmonary obstructive condition, etc. For example, a physician may preprogram the type of stimulation to provide (e.g., efferent stimulation and/or afferent-efferent stimulation), in order to treat the patient based upon the type of breathing disorder of the patient. The IMD 100 may then generate a signal, such as a pulse signal, to affect the operation of one or more portions of the pulmonary system of a patient.

The IMD 100 may then deliver the stimulation signal to the portion of the vagus nerve as determined by the factors such as an asthma condition, a constrictive pulmonary disorder condition, a cardiopulmonary obstructive condition, a pulse-oxygen percentage, etc. (block 730). The application of the electrical signal may be delivered to the main portion of the vagus nerve, to the bronchial branches of the vagus nerve, and/or to the pulmonary plexus. Application of the stimulation signal is designed to promote a blocking effect relating to a signal that is being sent from the brain to the various portions of the pulmonary system to treat the breathing disorder. For example, the hyper-responsiveness may be diminished by blocking various signals from the brain to the various portions of the lungs. This may be accomplished by delivering a particular type of controlled electrical signal, such as a controlled current signal to the pulmonary plexus. Additionally, afferent fibers may also be stimulated in combination with an efferent blocking to treat a pulmonary disorder.

Additional functions, such as a detection process, may be alternatively employed with the embodiment of the present invention. The detection process may be employed such as an external detection or an internal detection of a bodily function to adjust the operation of the IMD 100.

Figure 8:
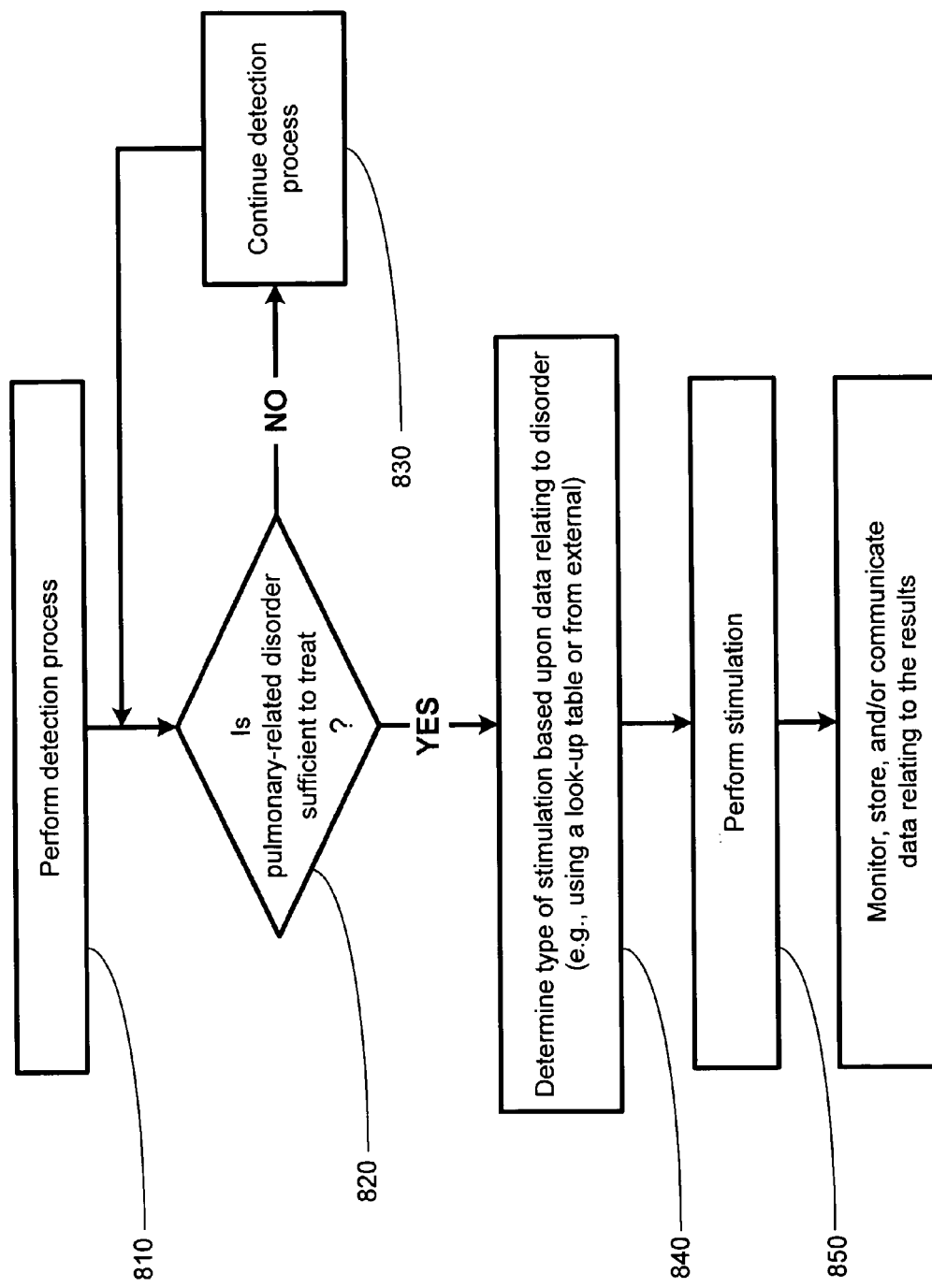
FIG. 8 illustrates a flowchart depiction of an alternative method for treating a pulmonary disease, in accordance with an alternative illustrative embodiment of the present invention.

Turning now to FIG. 8, a block diagram depiction of a method in accordance with an alternative embodiment of the present invention is illustrated. The IMD 100 may perform a database detection process (block 810). The detection process may encompass detecting a variety of types of characteristics of the pulmonary activity, such as respiratory rates, heart rate, pulse oxygen levels, etc. A more detailed depiction of the steps for performing the detection process is provided in FIG. 9, and accompanying description below. Upon performing the detection process, the IMD 100 may determine whether a detected disorder is sufficiently severe to treat based upon the measurements performed during the detection process (block 820). For example, the respiratory rate may be detected to see if an asthma attack is present. Upon a determination that the disorder is insufficient to treat by the IMD 100, the detection process is continued (block 830).

Upon a determination that the disorder is sufficient to treat using the IMD 100, a determination as to the type of stimulation based upon data relating to the disorder, is made (block 840). The type of stimulation may be determined in a variety of manners, such as performing a look-up in a look-up table that may be stored in the memory 617. Alternatively, the type of stimulation may be determined by an input from an external source, such as the external unit 670 or an input from the patient. Further, determination of the type of stimulation may also include determining the location as to where the stimulation is to be delivered. Accordingly, the selection of particular electrodes, which may be used to deliver the stimulation signal, is made. A more detailed description of the determination of the type of stimulation signal is provided in FIG. 10 and accompanying description below.

Upon determining the type of stimulation to be delivered, the IMD 100 performs the stimulation by delivering the electrical signal to one or more selected electrodes (block 850). Upon delivery of the stimulation, the IMD 100 may monitor, store, and/or compute the results of the stimulation (block 860). For example, based upon the calculation, a determination may be made that adjustment(s) to the type of signal to be delivered for stimulation, may be performed. Further, the calculations may reflect the need to deliver additional stimulation. Furthermore, data relating to the results of a stimulation may be stored in memory 617 for later extraction and/or further analysis. Additionally, real time or near real time communications may be provided to communicate the stimulation result and/or the stimulation log to an external unit 670.

Figure 9:
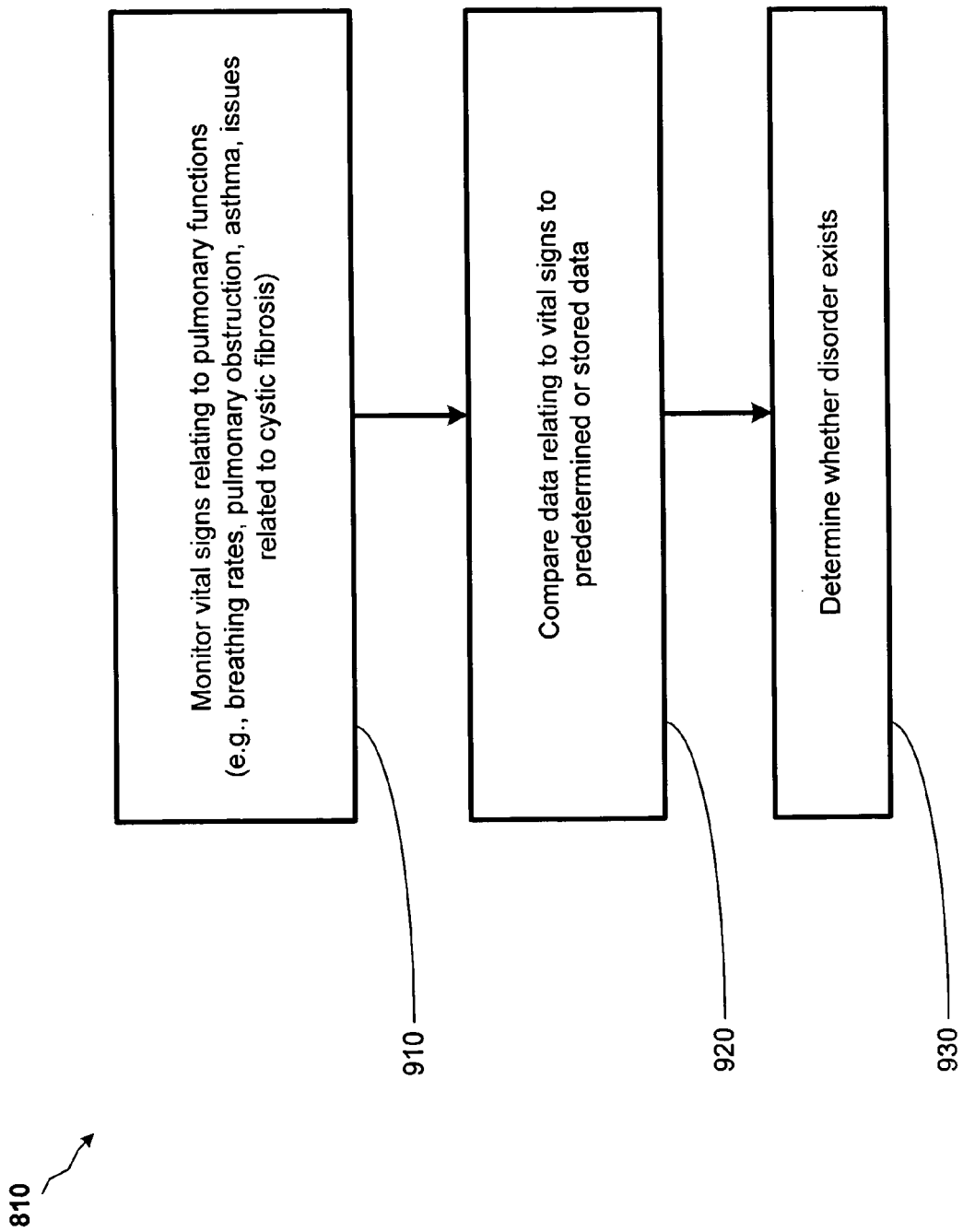
FIG. 9 depicts a more detailed flowchart depiction of step of performing a detection process of FIG. 8, in accordance with an illustrative embodiment of the present invention.

Turning now to FIG. 9, a more detailed block diagram depiction of the step of performing the detection process of block 810 in FIG. 8, is illustrated. The system 100 may monitor one or more vital signs relating to the pulmonary functions of the patient (block 910). For example, the breathing rates, the pulmonary obstruction level, asthma related activity, etc., may be detected. Other factors, such as breathing testing, heart rate, RSA, pulse oxygen levels, etc., may also be tested. This detection may be made by sensors residing inside the human body, which may be operatively coupled to the IMD. These factors may be also provided by an external device via the communication system 660.

Upon acquisition of various vital signs, a comparison may be performed comparing the data relating to the vital signs to predetermined, stored data (block 920). For example, the respiratory rates may be compared to various predetermined thresholds to determine whether aggressive action would be needed, or simply further monitoring would be sufficient. Based upon the comparison of the collected data with theoretical, stored thresholds, the IMD 100 may determine whether a disorder exists (block 930). For example, various vital signs may be acquired in order to determine afferent and/or efferent stimulation fibers are to be stimulated. Based upon the determination described in FIG. 9, the IMD 100 may continue to determine whether the disorder is sufficiently significant to perform treatment, as described in FIG. 8.

Figure 10:
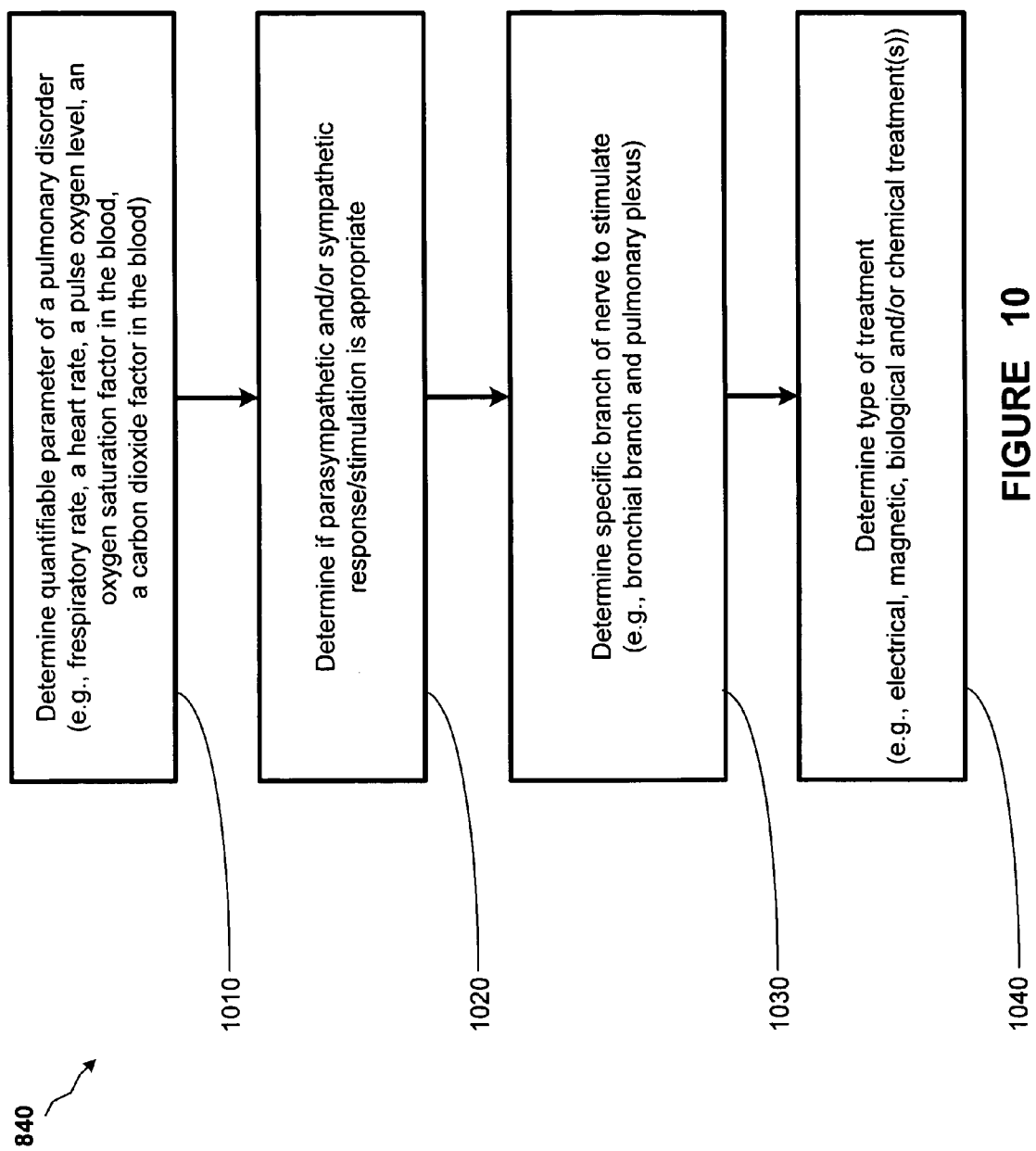
FIG. 10 depicts a more detailed flowchart depiction of the steps of determining a particular type of stimulation based upon data relating to a particular disorder described in FIG. 8, in accordance with an illustrative embodiment of the present invention.

Turning now to FIG. 10, a more detailed flowchart depiction of the step of determining the type of stimulation indicated in block 840 of FIG. 8, is illustrated. The IMD 100 may determine a quantifiable parameter of a breathing disorder (block 1010). These quantifiable parameters, for example, may include a frequency of occurrence of various symptoms of a disorder, e.g., tightening of the passageways, the severity of the disorder, a binary type of analysis as to whether a disorder or a symptom exists or not, a physiological measurement or detection, or other test results, such as a breathing test. Based upon these quantifiable parameters, a determination may be made whether a parasympathetic or a sympathetic response/stimulation is appropriate (block 1020). For example, as illustrated in Table 2, a matrix may be used to determine whether a parasympathetic or a sympathetic response for stimulation is appropriate. This determination may be overlaid by the decision regarding whether a blocking type of stimulation or a non-blocking type of stimulation should be performed.

TABLE 2

|  | BLOCKING | NON-BLOCKING |
| --- | --- | --- |
| PARASYMPATHETIC | Yes | No |
| SYMPATHETIC | No | Yes |

The example illustrated in Table 2 shows that a blocking parasympathetic stimulation is to be provided in combination with a sympathetic non-blocking stimulation for a particular treatment. A determination may be made that for a particular type of quantifiable parameter that is detected, the appropriate treatment may be to perform a parasympathetic blocking signal in combination with a sympathetic non-blocking signal. Other combinations relating to Table 2 may be implemented for various types of treatments. Various combinations of matrix, such as the matrix illustrated in Table 2 may be stored in the memory for retrieval by the IMD 100.

Additionally, external devices may perform such calculation and communicate the results and/or accompanying instructions to the IMD 100. The IMD 100 may also determine the specific batch of the nerve to stimulate (block 1030). For example, for a particular type of stimulation to be performed, the decision may be made to stimulate the pulmonary plexus and/or the bronchial branches of the vagus nerve. The IMD 100 may also indicate the type of treatment to be delivered. For example, an electrical treatment alone or in combination with another type of treatment may be provided based upon the quantifiable parameter(s) that are detected (block 1040). For example, a determination may be made that an electrical signal by itself is to be delivered. Alternatively, based upon a particular type of disorder, a determination may be made that an electrical signal, in combination with a magnetic signal, such as transcranial magnetic stimulation (TMS) may be performed. The determination of block 1040 may also include a decision to perform a blocking function that may include performing an electrical blocking and/or a chemical blocking (e.g., using a pharmaceutical compound, such as an anesthetic or steroid compound).

In addition to electrical and/or magnetic stimulation, a determination may be made whether to deliver a chemical, biological, and/or other type of treatment(s) in combination with the electrical stimulation provided by the IMD 100. In one example, electrical stimulation may be used to enhance the effectiveness of a chemical agent. Therefore, various drugs or other compounds may be delivered in combination with an electrical stimulation or a magnetic stimulation. Based upon the type of stimulation to be performed, the IMD 100 delivers the stimulation to treat various pulmonary disorders.

Utilizing the embodiments of the present invention, various types of stimulation may be performed to treat pulmonary disorders. For example, asthma, constrictive pulmonary disorder, cardiopulmonary obstructive disorders, etc, may be treated by the performing vagus nerve stimulation described herein. Embodiments of the present invention provides for performing pre-programmed delivery of stimulation and/or real time decisions relating to delivering stimulation. For example, various detections of parameters, such as respiratory rate, external input relating to physiological data, breathing testing, heart rate, RSA, pulse oxygen results, etc., may be used to determine whether a stimulation is needed and/or the type of stimulation to be delivered. Parasympathetic, sympathetic, blocking, non-blocking afferent, and/or efferent delivery of stimulation may be performed to treat pulmonary disorders.

All of the methods and apparatus disclosed and claimed herein may be made and executed without undue experimentation in light of the present disclosure. While the methods and apparatus of this invention have been described in terms of particular embodiments, it will be apparent to those of skill in the art that variations may be applied to the methods and apparatus and in the steps or in the sequence of steps of the method described herein without departing from the concept, spirit and scope of the invention as defined by the appended claims. It should be especially apparent that the principles of the invention may be applied to selected cranial nerves other than the vagus nerve to achieve particular results.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method of treating a patient having a pulmonary disorder, comprising:

coupling a first set of electrodes to a first nerve selected from a bronchial branch of a left vagus nerve and a pulmonary plexus;

coupling a second set of electrodes to a second nerve selected from a bronchial branch of a right vagus nerve and the pulmonary plexus;

activating the first set of electrodes to deliver energy from the first set of electrodes to a first target location on the first nerve to provide blocking parasympathetic nerve signals in combination with non-blocking sympathetic stimulation signals at the first target location to prevent the parasympathetic nerve signals from traveling between the brain and a first portion of the lungs through said first nerve sufficiently to reduce bronchial obstruction in the first portion of the lungs; and activating the second set of electrodes to deliver energy from the second set of electrodes to a second target location on the second nerve to provide blocking parasympathetic nerve signals in combination with non-blocking sympathetic stimulation signals at the second target location to prevent the parasympathetic nerve signals from travelling between the brain and a second portion of the lungs through said second nerve sufficiently to reduce bronchial obstruction in the second portion of the lungs.

2. The method of claim 1, wherein said pulmonary disorder comprises at least one of an asthma condition, constrictive pulmonary disorder, and a cardio pulmonary obstructive disorder.

3. The method of claim 1, wherein the energy causes efferent hyperpolarization on the first and second nerves.

4. The method of claim 1, wherein applying the energy comprises generating efferent action potentials in combination with afferent action potentials.

5. The method of claim 1, further comprising:
providing at least one programmable electrical signal generator;
coupling the at least one programmable electrical signal generator to the sets of electrodes; and
generating the energy with the at least one programmable electrical signal generator.

6. The method of claim 5, further comprising programming the at least one programmable electrical signal generator to define the energy by at least one parameter selected from a current magnitude, a pulse frequency, a pulse width, an on-time, and an off-time, wherein said at least one parameter is selected to treat the pulmonary disorder.

7. The method of claim 1, further comprising:
detecting a symptom of the pulmonary disorder, wherein the symptom comprises a breathing parameter of the patient; and
wherein the operation of applying the energy is initiated in response to detecting said symptom.

8. The method of claim 7, wherein the breathing parameter comprises at least one attribute selected from a respiration rate, a pulse oxygen level, an oxygen saturation factor in the blood, and a carbon dioxide factor in the blood.

9. The method of claim 1, wherein:
activating the first and second sets of electrodes includes applying the energy during a first treatment period to treat a chronic aspect of the pulmonary disorder; and
said method further comprises applying additional energy to the vagus nerve using the first and second sets of electrodes during a second treatment period to treat an acute aspect of the pulmonary disorder.

10. The method of claim 9, further comprising:
detecting a symptom of said pulmonary disorder,
wherein the symptom comprises a breathing parameter of the patient;
wherein the breathing parameter comprises at least one attribute selected from a respiration rate, a pulse oxygen level, an oxygen saturation factor in the blood, and a carbon dioxide factor in the blood; and
wherein the second treatment period is initiated in response to said step of detecting a symptom of the pulmonary disorder.

11. A method of treating a patient having a pulmonary disorder, comprising:
coupling a first set of electrodes to a first nerve selected from a bronchial branch of a left vagus nerve and a pulmonary plexus;
coupling a second set of electrodes to a second nerve selected from a bronchial branch of a right vagus nerve and the -a pulmonary plexus providing at least one electrical signal generator;
coupling the electrical signal generator to the first and second sets of electrodes;
detecting a symptom of the pulmonary disorder, wherein the symptom comprises at least one breathing parameter selected from respiration rate, pulse oxygen level, an oxygen saturation factor in the blood, and a carbon dioxide factor in the blood;
generating electrical signals with the electrical signal generator in response to detecting the symptom;
applying the electrical signals to the first set of electrodes to deliver energy from the first set of electrodes to the first nerve to provide blocking parasympathetic nerve signals in combination with non-blocking sympathetic stimulation signals at a first target location on the first nerve to prevent the parasympathetic nerve signals from travelling between the brain and a first portion of the lungs through said first nerve sufficiently to reduce bronchial obstruction in the first portion of the lungs; and
applying the electrical signals to the second set of electrodes to deliver energy from the second set of electrodes to the second nerve to provide blocking parasympathetic nerve signals in combination with non-blocking sympathetic stimulation signals at a second target location on the second nerve to prevent the parasympathetic nerve signals from travelling between the brain and a second portion of the lungs through said second nerve sufficiently to reduce bronchial obstruction in the second portion of the lungs.

12. The method of claim 11, further comprising:
programming the electrical signal generator to define the electrical signals by a plurality of parameters selected from a current magnitude, a pulse width, a pulse frequency, an on-time, and an off-time.

13. The method of claim 11, wherein:
the electrical signals are applied to the first and second sets of electrodes during a first treatment period to treat a chronic aspect of the pulmonary disorder and
the method further comprising applying additional electrical signals to the vagus nerve using the first and second sets of electrodes during a second treatment period to treat an acute aspect of the pulmonary disorder.

14. The method of claim 11, wherein:
the detection of the symptom of the pulmonary disorder is performed at least in part by the patient; and
the electrical signals are applied to the first and second sets of electrodes, at least in part, in response to input from the patient.

15. The method of claim 7, wherein:
the detection of the symptom of the pulmonary disorder is performed at least in part by the patient; and
the electrical signals are applied to the first and second electrodes, at least in part, in response to input from the patient.

16. A method of treating a patient having a pulmonary disorder, comprising:
coupling a first set of electrodes to a first nerve selected from a bronchial branch of a left vagus nerve and a pulmonary plexus;
coupling a second set of electrodes to a second nerve selected from a bronchial branch of a right vagus nerve and the pulmonary plexus;
detecting a symptom of the pulmonary disorder, wherein the symptom comprises a breathing parameter of the patient; and
in response to detecting the symptom of the pulmonary disorder, activating the first set of electrodes to deliver energy from the first set of electrodes to the first nerve to provide blocking parasympathetic nerve signals in combination with non-blocking sympathetic stimulation signals at a first target location on the first nerve to prevent the parasympathetic nerve signals from travelling between the brain and a first portion of the lungs through said first nerve sufficiently to reduce bronchial obstruction in the first portion of the lungs, and activating the second set of electrodes to deliver energy from the second set of electrodes to the second nerve to provide blocking parasympathetic nerve signals in combination with non-blocking sympathetic stimulation signals at a second target location on the second nerve to prevent the parasympathetic nerve signals from travelling between the brain and a second portion of the lungs through said second nerve sufficiently to reduce bronchial obstruction in the second portion of the lungs.

17. The method of claim 16, wherein the breathing parameter comprises at least one attribute selected from respiration rate;
pulse oxygen level;
an oxygen saturation factor in the blood; and
a carbon dioxide factor in the blood.

* * * * *